United States Patent
Harada et al.

(10) Patent No.: US 7,649,686 B2
(45) Date of Patent: Jan. 19, 2010

(54) BOX-TYPE MICROSCOPE APPARATUS

(75) Inventors: Mitsuo Harada, Hachioji (JP);
Yoshihiro Shimada, Sagamihara (JP)

(73) Assignee: Olympus Corporation, Tokyo (JP)

( * ) Notice: Subject to any disclaimer, the term of this patent is extended or adjusted under 35 U.S.C. 154(b) by 30 days.

(21) Appl. No.: 12/141,371

(22) Filed: Jun. 18, 2008

(65) Prior Publication Data
US 2009/0185268 A1    Jul. 23, 2009

(30) Foreign Application Priority Data
Jun. 20, 2007  (JP) ............... 2007-162591

(51) Int. Cl.
*G02B 21/26* (2006.01)
(52) U.S. Cl. ............................................. 359/391
(58) Field of Classification Search .......... 359/391–395
See application file for complete search history.

(56) References Cited

U.S. PATENT DOCUMENTS 7,382,531 B2 *   6/2008   Tsuchiya et al. ............. 359/395
2005/0282268 A1 *  12/2005  Kagayama ............... 435/288.7
2006/0072190 A1 *  4/2006   Okugawa ..................... 359/368
2007/0065936 A1 *  3/2007   Hasegawa et al. ......... 435/288.7
2009/0046358 A1 *  2/2009   Shimada ..................... 359/381
2009/0141345 A1 *  6/2009   Tsuchiya ..................... 359/393

FOREIGN PATENT DOCUMENTS

JP           2003005079           1/2003

* cited by examiner

*Primary Examiner*—Alessandro Amari
*Assistant Examiner*—Mark Consilvio
(74) *Attorney, Agent, or Firm*—Pillsbury Winthrop Shaw Pittman, LLP

(57) ABSTRACT

A box-type microscope apparatus includes a stage, a microscope, and a housing, which has a fixed housing and a moving housing provided to be openable, closable, and movable with respect to the fixed housing. The box-type microscope apparatus further includes a specimen vessel positioning device for fixing the specimen vessel placed on the stage at a constant position. of the stage and a positioning release device for actuating the specimen vessel positioning means when the moving housing is moved toward a position of a closed state to release a positioning of the specimen vessel performed by the specimen vessel positioning device with respect to the stage when the moving housing is opened.

12 Claims, 15 Drawing Sheets

FIG.16A
FIG.16B
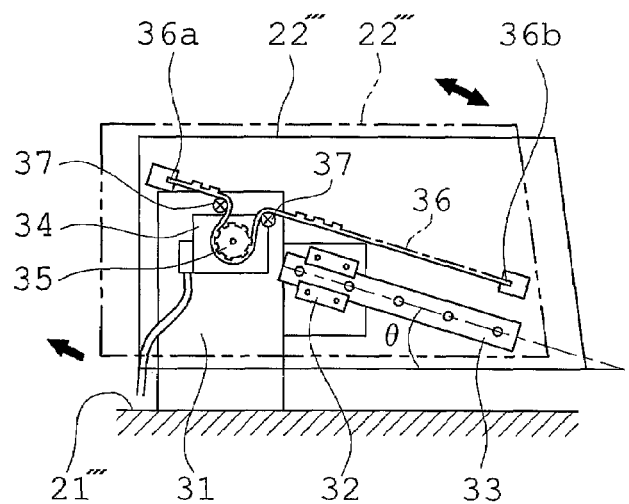
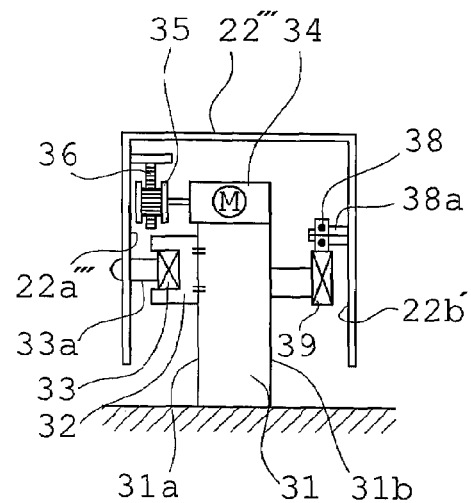

BOX-TYPE MICROSCOPE APPARATUS

This application claims benefits of Japanese Patent Application No. 2007-162591 filed in Japan on Jun. 20, 2007, the contents of which are incorporated herein by reference.

BACKGROUND OF THE INVENTION

1. Field of the Invention

This invention relates to a box-type microscope apparatus, such as an optical microscope apparatus, having a housing for blocking light or protecting a specimen environment which is chiefly used for the purpose of the observation and/or measurement of a living specimen such as a cell.

2. Description of Related Art

Optical microscopes are generally used as means for observing living cells, in vivo, such as medium cell specimens, cultured with culture fluid on petri dishes or microplates. In recent years, the optical microscope has been combined with a high-sensitivity image pickup means, such as a cooled CCD camera, so that feeble fluorescent light is detected from the medium cell labeled by fluorescence and is recorded as image data. The fluorescent light from the medium cell labeled by fluorescence is extremely feeble, and in order to detect this feeble fluorescent light with accuracy, the detection of light other than the fluorescent light from the cell, namely, of disturbance light, must be prevented as far as possible. For this, some optical microscope apparatuses commercially available have structures such that the entire inverted microscope is covered with a housing and thereby external light is not detected at least when an image is acquired. As one of such box-type optical microscope apparatuses, an inverted microscope, for example, made by General Electric Healthcare Company, is available.

This optical microscope apparatus covers the entire inverted microscope with a housing and includes an electric stage on which a microplate can be placed and which is controlled by a computer and thereby can be moved in X and Y directions. The housing is partially provided with a door so that the electric stage springs forth from the door to a preset position outside the housing, with the microplate placed on the stage. An operator brings about a state where the electric stage lies at the preset position outside the housing and is capable of replacing or setting the microplate. In accordance with instructions of the operator, the door is such as to open when the electric stage springs forth to the preset position outside the housing and to close when the electric stage is incorporated in the housing. Whereby, the entire inverted microscope can be light-blocked and it becomes possible to protect the specimen environment in combination with a living body holding device such as a temperature controller.

In such a box-type motor-operated microscope, when an observation object is moved from a position outside the box to an observation position inside the box by the electric stage, there is the possibility that foreign matter, such as the hand and finger of the operator, is drawn in error into the box, and thus it becomes necessary to ensure safety. However, in an upright box-type microscope incorporating an image forming optical system, an observation optical system, and the electric stage in the housing, the safety mechanism of a door section is known (for example, refer to Japanese Patent Kokai No. 2003-5079). The microscope apparatus disclosed in Kokai No. 2003-5079 is provided with a detection means for detecting the presence of the foreign matter in the door section when a supporting bench supporting the observation object is brought into the housing.

However, the present applicant has invented an optical microscope apparatus set forth in the specification of Japanese Patent Application No. 2005-331325, as the box-type motor-operated microscope for the purpose of obviating oversizing of the apparatus and improving the operation accuracy of the stage without enlarging the operation range of the stage. An optical microscope apparatus 101 according to this invention, for example, as shown in FIG. 1, includes an inverted microscope 102 having an electric stage 112 on which a microplate 140 incorporating a specimen A is placed, a transmitting illumination optical system 111, and an image forming optical system 114; and a housing 120 surrounding the inverted microscope 102. The housing 120 is composed of a fixed housing 121 and a moving housing 122 which can be opened and closed with respect to the fixed housing 121. The moving housing 122 is rotatably supported by the fixed housing 121 so as to bring about an opened state shown in FIG. 1 by rotating on a rotary shaft 160 through a rotation mechanism, not shown, like bearings. The housing 120 is such that, in a closed state, external light is blocked and the inverted microscope 102 can be maintained in a light-blocked state. Also, in this figure, reference numeral 113 denotes a reflecting illumination optical system.

Of optical parts constituting the transmitting illumination optical system 111 and the image forming optical system 114, some optical parts arranged above the electric stage 112 are provided to be movable through the moving housing 122. When the moving housing 122 is located at the position of the opened state with respect to the fixed housing 121, these optical parts are removed from the upper position of the electric stage 112, while when it is located at the position of the closed state, the optical axis of the transmitting illumination optical system 111 is practically aligned with that of the image forming optical system 114.

According to the optical microscope apparatus 101 constructed as mentioned above, in the case where the microplate 140 incorporating the specimen A on the electric stage 112 is replaced, when the moving housing 122 is opened with respect to the fixed housing 121, some optical parts in the transmitting illumination optical system arranged above the electric stage 112 are removed, together with the moving housing 122, from the upper position of the electric stage 112. Hence, a wide space is ensured above the electric stage 112 and the work of the replacement and fixing of the specimen is facilitated. When the moving housing 122 is closed with respect to the fixed housing 121, the inverted microscope 102 is covered with the housing 120 and is light-blocked, and the optical axis of the optical system located above the electric stage 112 constituting the inverted microscope 102 is practically aligned with that of the optical system located below the electric stage 112, so that it becomes possible to utilize illumination light from the transmitting illumination optical system 111 and to carry out a microscope observation through the image forming optical system 114.

An optical microscope apparatus 201 of another example set forth in the specification of Application No. 2005-331325, as shown in FIGS. 2A and 2B, is constructed so that a housing 220 is provided with a moving housing 222 movable in a horizontal direction through a direct-acting guide, not shown, on a fixed housing 221. Between the fixed housing 221 and the moving housing 222, a click mechanism, not shown, is provided so that the moving housing 222 is capable of maintaining the opened and closed states with respect to the fixed housing 221. In these figures, reference numeral 211 denotes a transmitting illumination optical system; 212, an electric stage; 213, an image forming lens; 214, an image forming optical system; and 219, a condenser lens.

According to the optical microscope apparatus 201 of FIGS. 2A and 2B constructed as mentioned above, when the moving housing 222, as shown in FIG. 2A, is located at the position of the closed state with respect to the fixed housing 221, the optical axis of the condenser lens 219 in the transmitting illumination optical system 211 provided in the moving housing 222 is practically aligned with that of the objective lens 213 and the moving housing 222 is maintained in a fixed state by the operation of the click mechanism at this position, so that a space inside the housing 220 is blocked from the external light. On the other hand, as shown in FIG. 2B, when the moving housing 222 is moved to be in the opened state, optical members arranged above the electric stage 212 in the transmitting illumination optical system 211 are removed together with the moving housing 222. Consequently, a wide space is ensured above the electric stage 112 and the work of the replacement and fixing of the specimen is facilitated. Moreover, the correction collar of the objective lens can also be operated.

According to the optical microscope apparatus 201 of FIGS. 2A and 2B, the housing 220 can be opened and closed only by sliding the moving housing 222 in the horizontal direction with respect to the fixed housing 221 and a great force is not needed for manipulation. Hence, there is the advantage that maneuverability is excellent. In addition, according to the optical microscope apparatuses shown in FIGS. 2A and 2B, since there is no need to enlarge the operation range of the electric stage to the exterior of the housing in order to ensure a wide space for the work of the replacement of the specimen above the electric stage, oversizing of the apparatus can be prevented and the operation accuracy of the electric stage can be improved.

SUMMARY OF THE INVENTION

The box-type microscope apparatus according to the present invention comprises a microscope having a stage for placing a specimen vessel thereon, a transmitting illumination optical system, and an image forming optical system; a housing surrounding the microscope, the housing including a fixed housing and a moving housing provided to be openable, closable, and movable with respect to the fixed housing; and a switching mechanism in which, of optical parts constituting the transmitting illumination optical system or the image forming optical system, at least partial optical parts arranged above the stage are provided to be movable so that when the moving housing is located at a position of an opened state with respect to the fixed housing, the partial optical parts are removed from the optical axis of another optical system, while when the moving housing is located at a position of a closed state, optical axes of both optical systems are aligned with each other. The box-type microscope apparatus of the present invention further comprises a specimen vessel positioning means for fixing the specimen vessel placed on the stage to a constant position of the stage; and a positioning release means for actuating the specimen vessel positioning means when the moving housing is moved from the position of the opened state toward the position of the closed state with respect to the fixed housing and for releasing a positioning of the specimen vessel performed by the specimen vessel positioning means with respect to the stage when the moving housing is located at the position of the opened state with respect to the fixed housing.

In the box-type microscope apparatus of the present invention, it is desirable that the specimen vessel positioning means has a bumping part on which side surfaces of the specimen vessel placed on the stage are allowed to abut from X and Y directions and a specimen vessel pressing means for pressing a preset corner of the specimen vessel placed on the stage to make the side surface of the specimen vessel abut on the bumping part.

In the box-type microscope apparatus of the present invention, it is desirable that the specimen vessel pressing means is a clamp lever including a shaft provided to the stage; a lever body rotatably supported by the shaft, provided with a pressing part allowing the preset corner of the specimen vessel to be pressed; and a spring whose one end is connected to the lever body and whose remaining end is connected to the stage, applying a force to the lever body in a direction in which the preset corner of the specimen vessel is pressed.

In the box-type microscope apparatus of the present invention, it is desirable that the positioning release means includes an engagement part provided to the specimen vessel pressing means; a specimen vessel pressing release means for pressing the engagement part to be releasable with respect to the pressing of the specimen vessel applied by the specimen vessel pressing means, the specimen vessel pressing release means being provided to a preset part of the housing to allow a pressing; and an actuation part of the specimen vessel pressing release means releasing the pressing on the specimen vessel applied by the specimen vessel pressing means through the specimen vessel pressing release means by pressing the specimen vessel pressing release means so that when the moving housing is located at the position of the opened state with respect to the fixed housing, a release from the pressing on the specimen vessel applied by the specimen vessel pressing means is completed through the specimen vessel pressing release means.

In the box-type microscope apparatus of the present invention, it is desirable that the specimen vessel pressing release means is a release lever including a shaft provided to the fixed housing; a lever body rotatably supported by the shaft, provided at one end with a pressing part allowing the engagement part provided to the specimen vessel pressing means to be pressed; and a spring whose one end is connected to the lever body and whose remaining end is connected to the fixed housing, applying a force to the lever body in a direction in which the pressing on the engagement part provided to the specimen vessel pressing means is released, and the actuation part of the specimen vessel pressing release means allows an end opposite to the pressing part of the release lever to be pressed.

In the box-type microscope apparatus of the present invention, it is desirable that the specimen vessel pressing release means is a release lever including a shaft provided to the stage; a lever body rotatably supported by the shaft, provided at one end with a pressing part allowing the engagement part provided to the specimen vessel pressing means to be pressed; and a spring whose one end is connected to the lever body and whose remaining end is connected to the stage, applying a force to the lever body in a direction in which the pressing on the engagement part provided to the specimen vessel pressing means is released, and the actuation part of the specimen vessel pressing release means allows an end opposite to the pressing part of the release lever to be pressed.

In the box-type microscope apparatus of the present invention, the moving housing may be mounted to be movable in a direction horizontal with respect to the fixed housing.

In the box-type microscope apparatus of the present invention, the moving housing may be mounted to be movable parallel to an oblique direction with respect to the fixed housing.

In the box-type microscope apparatus of the present invention, the moving housing may be mounted to be rotatable, with a rotary axis as a center, with respect to the fixed housing.

In the box-type microscope apparatus of the present invention, it is desirable that the actuation part of the specimen vessel pressing release means includes a projection provided to the moving housing.

In the box-type microscope apparatus of the present invention, it is desirable that the actuation part of the specimen vessel pressing release means includes a plate-shaped projection having a preset length in a vertical direction and provided to the moving housing, and when the moving housing is moved parallel to an oblique direction with respect to the fixed housing, a part of the plate-shaped projection pressing an end opposite to the pressing part of the release lever is displaced along a vertical direction.

In the box-type microscope apparatus of the present invention, it is desirable that the actuation part of the specimen vessel pressing release means includes a plate-shaped member having a preset length whose one end is mounted to be rotatable on a rotary axis with respect to the moving housing and whose remaining end is mounted to be guidable at least in a horizontal direction through a guide member provided to the fixed housing so that when the moving housing is rotated on a rotary axis with respect to the fixed housing, a part of the plate-shaped member pressing an end opposite to the pressing part of the release lever is displaced along a longitudinal direction.

According to the present invention, the box-type microscope apparatus is obtained which is low in cost and simple in design and allows the specimen vessel to be easily placed at the optimum position without making the positional adjustment of the specimen vessel on the stage in replacing the specimen vessel and the specimen vessel to be replaced readily and rapidly.

These and other features and advantages of the present invention will become apparent from the following detailed description of the preferred embodiments when taken in conjunction with the accompanying drawings.

BRIEF DESCRIPTION OF THE DRAWINGS

FIGS. 16A and 16B are explanatory views showing a movement mechanism of the moving housing in the box-type microscope apparatus of FIG. 14, which are a side view and a front view, respectively.

DETAILED DESCRIPTION OF THE PREFERRED EMBODIMENTS

Before undertaking the description of the embodiments, the function and effect of the present invention will be explained.

The box-type microscope apparatus of the present invention comprises a microscope having a stage for placing a specimen vessel thereon, a transmitting illumination optical system, and an image forming optical system; a housing surrounding the microscope, the housing including a fixed housing and a moving housing provided to be openable, closable, and movable with respect to the fixed housing; and a switching mechanism in which, of optical parts constituting the transmitting illumination optical system or the image forming optical system, at least partial optical parts arranged above the stage are provided to be movable so that when the moving housing is located at a position of an opened state with respect to the fixed housing, the partial optical parts are removed from the optical axis of a remaining optical system, while when the moving housing is located at a position of a closed state, optical axes of both optical systems are aligned with each other.

The box-type microscope apparatus of the present invention further comprises a specimen vessel positioning means for fixing the specimen vessel placed on the stage at a constant position of the stage; and a positioning release means for actuating the specimen vessel positioning means when the moving housing is moved from the position of the opened state toward the position of the closed state with respect to the fixed housing and for releasing a positioning of the specimen vessel performed by the specimen vessel positioning means with respect to the stage when the moving housing is located at the position of the opened state with respect to the fixed housing.

When the specimen vessel positioning means is provided in this way, the positional adjustment that formerly has been made in placing the specimen vessel on an electric stage becomes unnecessary. It is also unnecessary that whenever the specimen vessel is placed on the electric stage, the position of the specimen vessel on the electric stage is detected through a relative position measuring means and the amount of operation of the electric stage is calculated in accordance with detected positional information. In addition, the specimen vessel need not be secured with screws and can be replaced without removing screws. According to the present invention, therefore, the box-type microscope apparatus is obtained which is low in cost and simple in design and allows the specimen vessel to be easily placed at the optimum position without making the positional adjustment of the specimen vessel on the stage in replacing the specimen vessel and the specimen vessel to be replaced readily and rapidly.

First Embodiment

Figure 1:
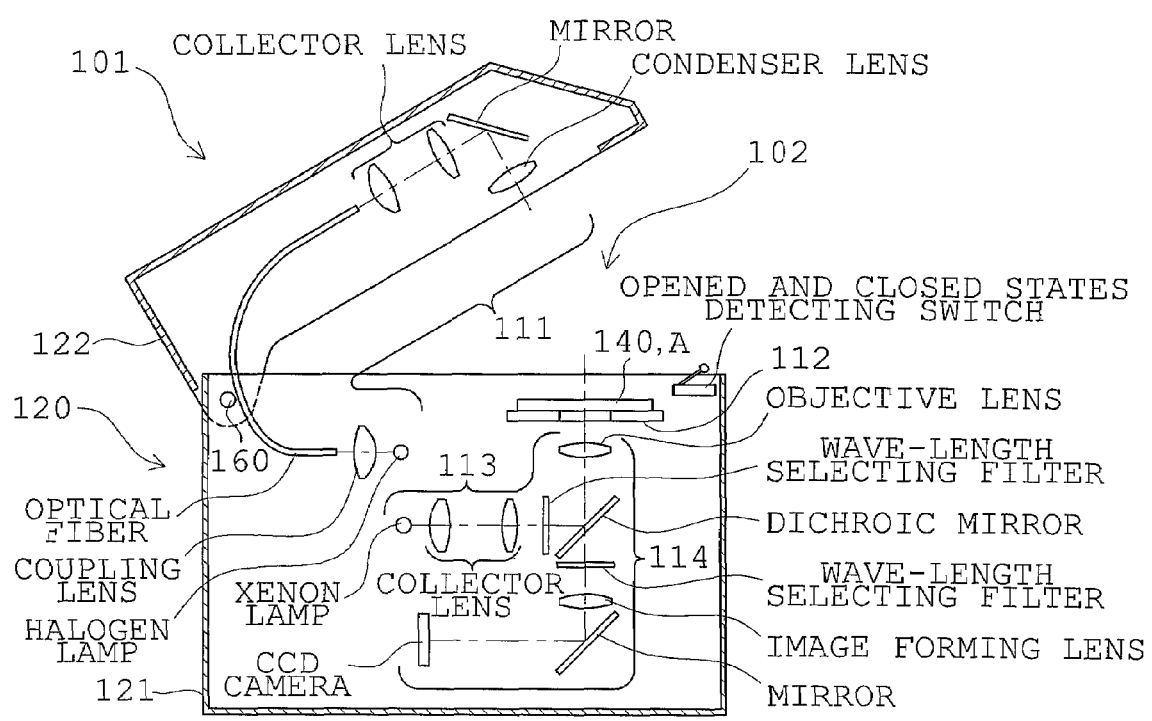
FIG. 1 is a sectional view taken along the optical axis, showing one example of a conventional box-type microscope apparatus.
Figure 2A:
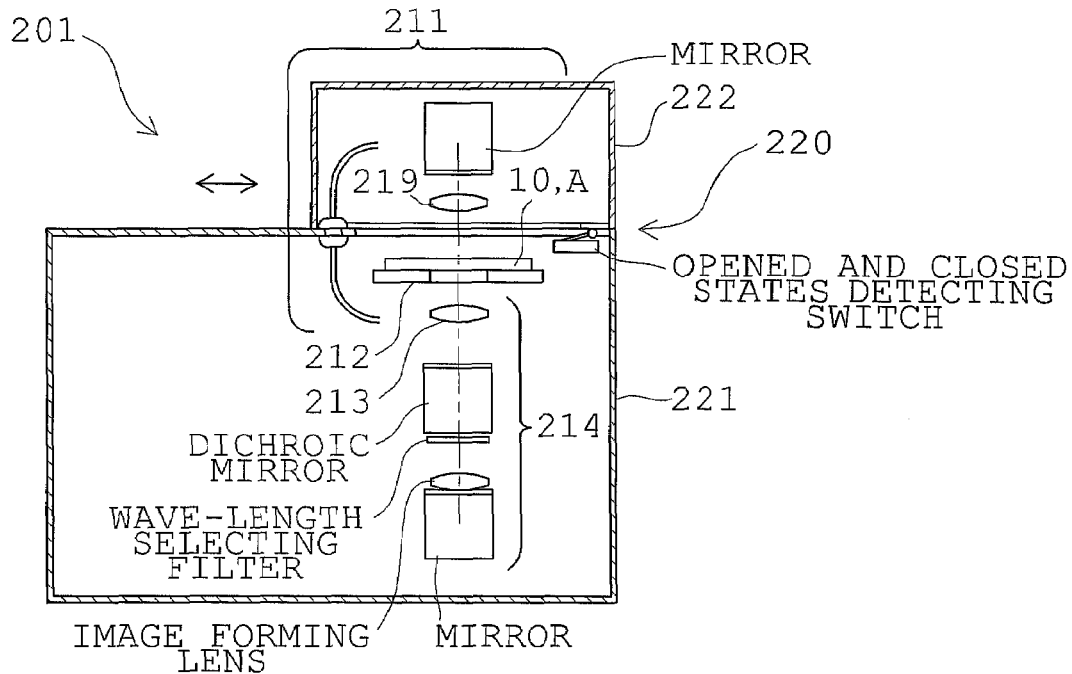
FIGS. 2A and 2B are sectional views taken along the optical axis, showing another example of the conventional box-type microscope apparatus in states where the moving housing is located at the positions of a closed state and an opened state, respectively.
Figure 2B:
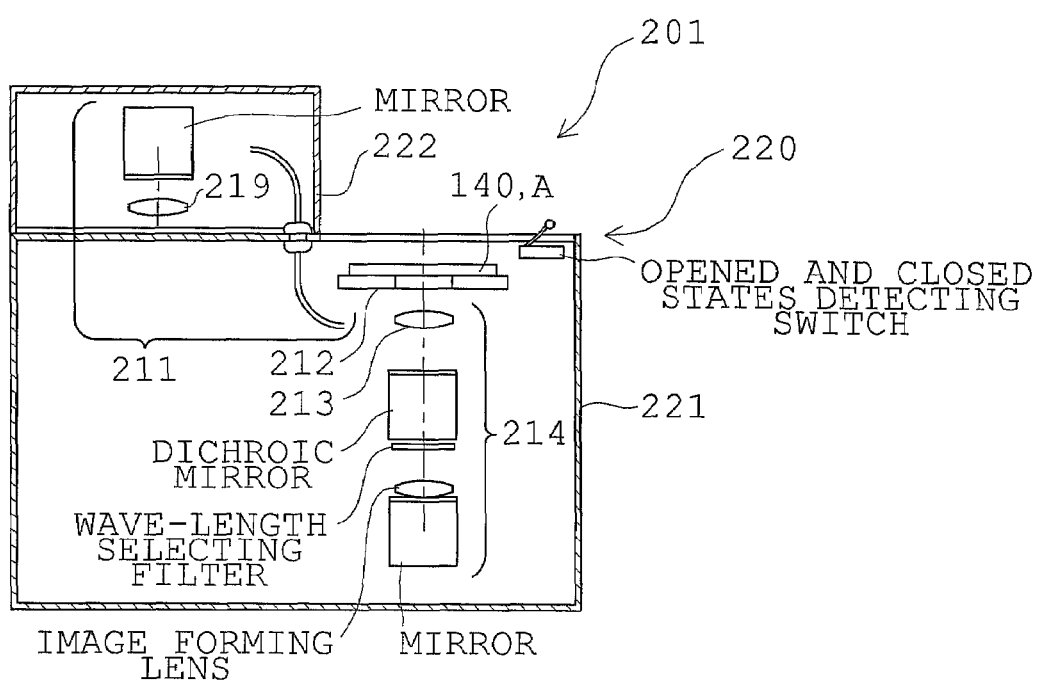
Figure 3:
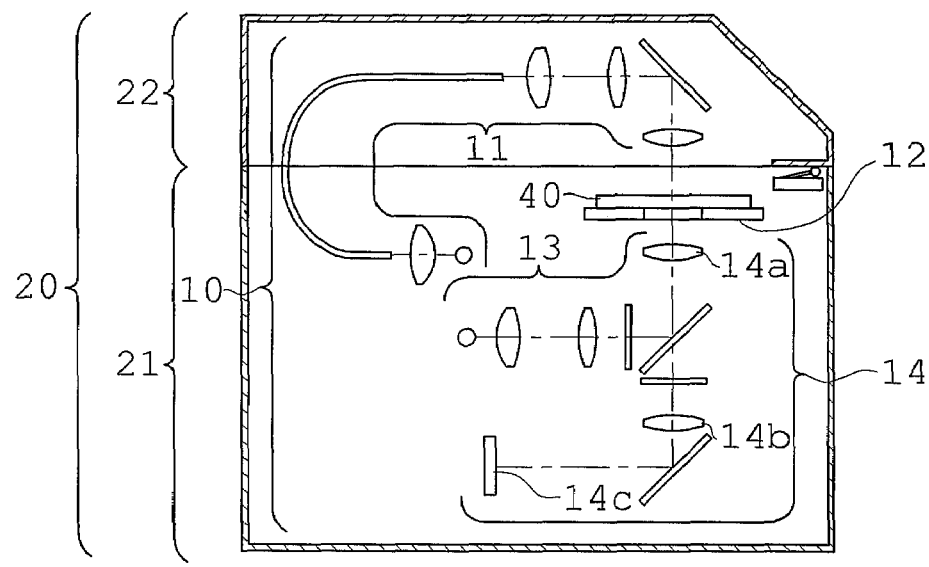
FIG. 3 is an explanatory view showing a schematic general structure of the box-type microscope apparatus according to a first embodiment in the present invention.
Figure 4:
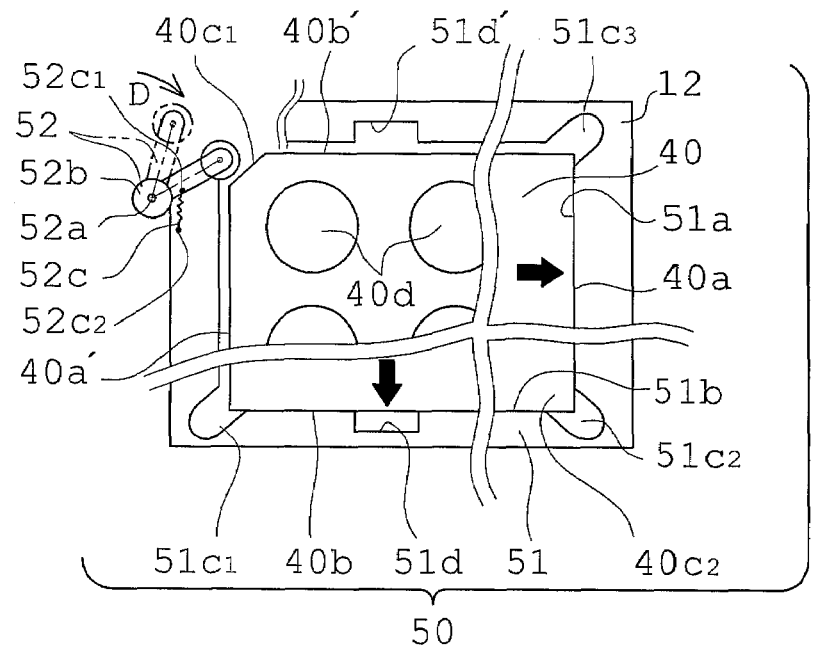
FIG. 4 is an explanatory view showing a fundamental structure of a specimen vessel positioning means that is an essential part of the box-type microscope apparatus of FIG. 3.
Figure 5:
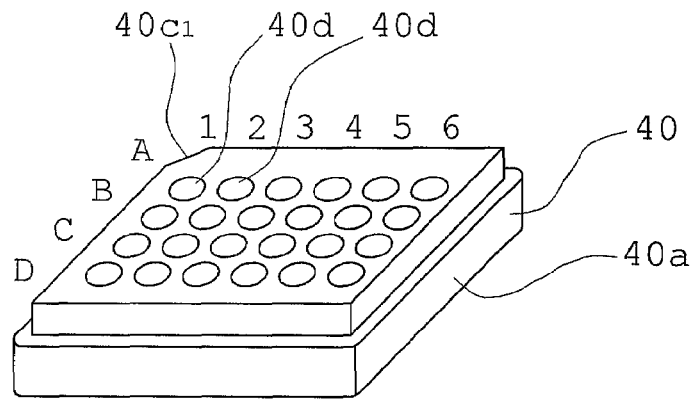
FIG. 5 is a perspective view showing the appearance of the specimen vessel used for the observation and/or measurement in the box-type microscope apparatus of the first embodiment.

FIG. 3 is an explanatory view showing a schematic general structure of the box-type microscope apparatus according to a first embodiment in the present invention and FIG. 4 is an explanatory view showing a fundamental structure of a specimen vessel positioning means that is an essential part of the box-type microscope apparatus of FIG. 3. FIG. 5 is a perspective view showing the appearance of the specimen vessel used for the observation and/or measurement in the box-type microscope apparatus of the first embodiment.

Figure 6:
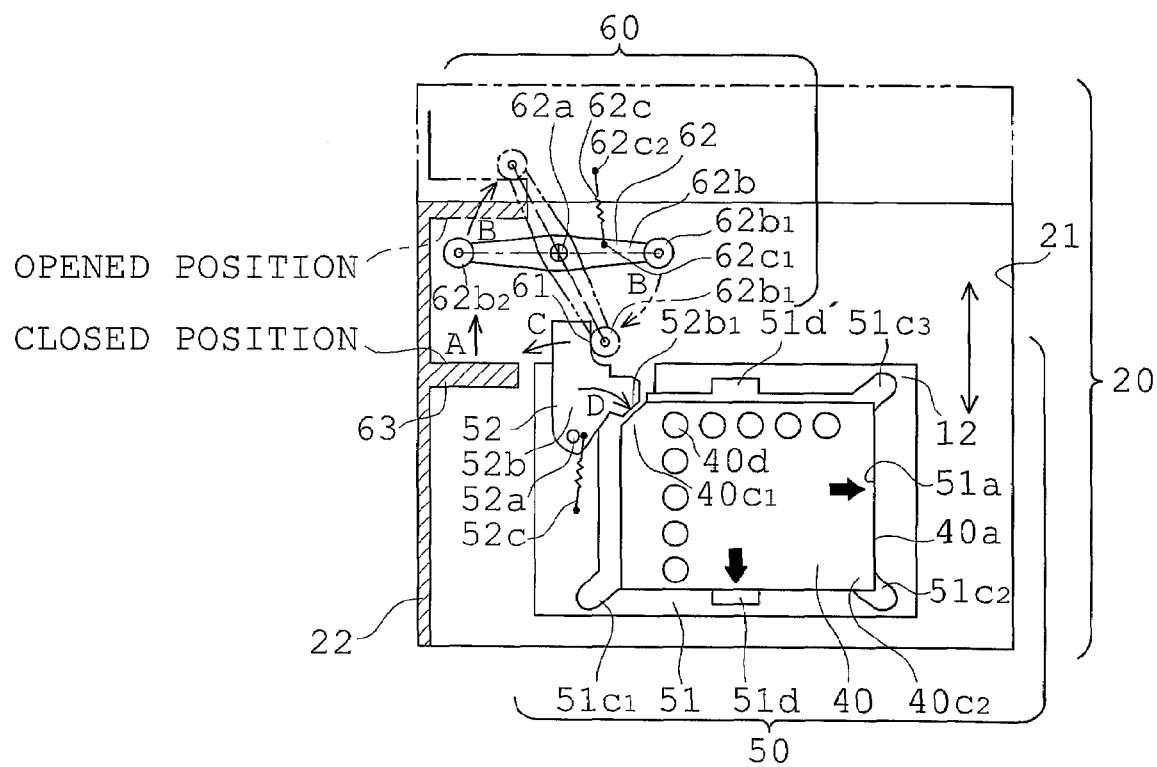
FIG. 6 is an explanatory view showing a fundamental structure of a positioning release means that is an essential part of the box-type microscope apparatus of FIG. 3.

FIG. 6 is an explanatory view showing a fundamental structure of a positioning release means that is an essential part of the box-type microscope apparatus of FIG. 3.

The box-type microscope apparatus of the first embodiment includes a microscope 10 and a housing 20 incorporating the microscope 10. The microscope 10 has a transmitting illumination optical system 11, an electric stage 12, a reflecting illumination optical system 13, and an image forming optical system 14. The transmitting illumination optical system 11 is constructed so that a specimen in a specimen vessel 40, for example, consisting of a microplate, placed on the electric stage 12 is irradiated with white light in a vertical direction from above. Also, in a specific optical arrangement of the transmitting illumination optical system 11, any arrangement in which the specimen in the specimen vessel 40 can be irradiated with the white light in a vertical direction from above is applicable.

The electric stage 12 is constructed so that the specimen vessel 40 can be placed thereon. The electric stage 12 is also constructed to be slidable in X and Y directions so that a desired part in the specimen vessel 40 (for example, a desired well in the microplate) can be moved to an observation position by the control of a computer (not shown) through a driving means (not shown). The reflecting illumination optical system 13 is placed below the electric stage 12 and is constructed so that the specimen in the specimen vessel 40 placed on the electric stage 12 is irradiated with excitation light in a vertical direction from blow. Also, in a specific optical arrangement of the reflecting illumination optical system 13, any arrangement in which the specimen in the specimen vessel 40 can be irradiated with the excitation light in a vertical direction from below is applicable.

The image forming optical system 14 has an objective lens 14a and an image forming lens 14b. In FIG. 3, reference numeral 14c represents a camera (for example, a CCD camera) for picking up the image of the specimen formed through the image forming lens 14b. Also, in a specific optical arrangement of the image forming optical system 14, any arrangement in which the objective lens 14a and the image forming lens 14b are provided and the image of the specimen can be formed at a preset image forming position is applicable.

The housing 20 is constructed with a fixed housing 21 and a moving housing 22. The fixed housing 21 is fixedly placed in a state where optical elements, containing the electric stage 12, arranged below the electric stage 12 are held. The moving housing 22 is constructed to be movable in directions of opened and closed states with respect to the fixed housing 21 while holding optical elements (the transmitting illumination optical system 11) arranged above the electric stage 12. The housing 20 is constructed so that the moving housing 22 is moved in a direction of an opened state by a preset amount and thereby the fixed housing 21 is opened and the specimen vessel 40 placed on the electric stage 12 is made replaceable, while the moving housing 22 is moved in a direction of a closed state to abut on the fixed housing 21 and thereby the microscope 10 is sealed and light-blocked in cooperation with the fixed housing 21 and the optical axis of the transmitting illumination optical system 11 is practically aligned with that of the image forming optical system 14.

Here, the box-type microscope apparatus of the first embodiment, as shown in FIGS. 4 and 6, has a specimen vessel positioning means 50 and a positioning release means 60. The specimen vessel positioning means 50, as shown in FIG. 4, is the means for fixing the specimen vessel 40 placed on the electric stage 12 at a constant position of the electric stage and is constructed to have a bumping part 51 and a specimen vessel pressing means 52. The specimen vessel 40, as illustrated in FIG. 5, is provided with a plurality of wells 40d arranged in a two-dimensional direction and is constructed with a microplate similar in contour to a rectangle. One corner $40c^1$ of the specimen vessel 40 is chamfered so that the specimen vessel 40 is easily pressed through the specimen vessel pressing means 52. The bumping part 51 is constructed with a frame-shaped member provided on the upper surface of the electric stage 12. The frame-shaped member 51 includes an X-direction bumping part 51a and a Y-direction bumping part 51b on its inside surface. The X-direction bumping part 51a and the Y-direction bumping part 51b are constructed so that side surfaces 40a and 40b of the specimen vessel 40 are capable of abutting on these bumping parts from the X and Y directions.

At corners of the inside surface of the frame-shaped member 51, notches $51c^1$, $51c^2$, and $51c^3$ are configured. The notch $51c^2$ prevents the positional shift and damage of the specimen vessel 40 that may be produced by interference between a corner $40c^2$ of the specimen vessel 40 and the corner of the frame-shaped member 51 when the side surfaces $40a$ and $40b$ of the specimen vessel 40 are made to abut on the bumping parts $51a$ and $51b$, respectively. Furthermore, at preset positions between corners on the inside surface of the frame-shaped member 51, a pair of notches $51d$ and $51d'$ is configured. The notches $51d$ and $51d'$ are configured into sizes such that a pair of side surfaces $40b$ and $40b'$ of the specimen vessel 40 placed inside the frame-shaped member 51 are held and the specimen vessel 40 is taken out.

The specimen vessel pressing means 52 is constructed with a clamp lever. The clamp lever 52 includes a shaft $52a$, a lever body $52b$, and a spring $52c$. The shaft $52a$ is provided close to a corner located on a diagonal line on which the X-direction bumping part $51a$ intersects with the Y-direction bumping part $51b$ on the electric stage 12. The lever body $52b$ is rotatably supported by the shaft $52a$. The lever body $52b$ is provided with a pressing part $52b^1$ capable of pressing the corner $40c^1$ of the specimen vessel 40. The spring $52c$ is such that its one end $52c^1$ is connected to the lever body $52b$ and a remaining end $52c^2$ is connected to the electric stage 12. The spring $52c$ is designed to apply a force to the lever body $52b$ in a direction in which the corner $40c^1$ of the specimen vessel 40 is pressed through the pressing part $52b^1$.

The positioning release means 60, as shown in FIG. 6, has an engagement part 61, a specimen vessel pressing release means 62, and an actuation part 63 of the specimen vessel pressing release means. The engagement part 61 is provided to the specimen vessel pressing means 52. The specimen vessel pressing release means 62 is constructed with a release lever including a shaft $62a$, a lever body $62b$, and a spring $62c$. The shaft $62a$ is provided to the fixed housing 21. The lever body $62b$ is rotatably supported by the shaft $62a$ and is provided with a pressing part $62b^1$ capable of pressing the engagement part 61 provided to the specimen vessel pressing means 52 at its one end. The spring $62c$ is such that its one end $62c^1$ is connected to the lever body $62b$ and a remaining end $62c^2$ is connected to the fixed housing 21. The spring $62c$ applies a force to the lever body $62b$ in a direction in which a pressing on the engagement part 61 provided to the specimen vessel pressing means 52 is released. The specimen vessel pressing release means 62 is constructed so that the engagement part 61 is pressed and thereby a pressing of the specimen vessel pressing means 52 on the specimen vessel 40 can be released.

The actuation part 63 of the specimen vessel pressing release means is provided at a preset position of the housing 20 (the moving housing 22 in FIG. 6) so that an end $62b^2$ opposite to the pressing part $62b^1$ of the release lever that is the specimen vessel pressing release means 62 can be pressed. The actuation part 63 of the specimen vessel pressing release means is constructed so that the specimen vessel pressing release means 62 (more specifically, the end $62b^2$) is pressed and thereby the pressing of the specimen vessel pressing means 52 on the specimen vessel 40 is released through the specimen vessel pressing release means 62, and when the moving housing 22 is located at the position of the opened state with respect to the fixed housing 21, a release from the pressing on the specimen vessel 40 applied by the specimen vessel pressing means 52 is completed through the specimen vessel pressing release means 62.

Also, the actuation part 63 of the specimen vessel pressing release means in the box-type microscope apparatus of the first embodiment is applicable to any of structures that the moving housing 22 is mounted to be movable in a horizontal direction with respect to the fixed housing 21, that it is mounted to be movable parallel to an oblique direction, and that it is mounted to be rotatable, with a rotary axis as a center. In the case of the structure that the moving housing 22 is mounted to be movable in the horizontal direction with respect to the fixed housing 21, the actuation part 63 of the specimen vessel pressing release means can be constructed by providing the moving housing 22 with a projection. In the structure that the moving housing 22 is mounted to be movable parallel to the oblique direction with respect to the fixed housing 21, the actuation part 63 of the specimen vessel pressing release means can be constructed in such a way that the moving housing 22 is provided with a plate-shaped projection having a preset length in a vertical direction, and when the moving housing 22 is moved parallel to the oblique direction with respect to the fixed housing 21, a part of the plate-shaped projection pressing an end opposite to the pressing part $62b1$ of the release lever is displaced along a vertical direction.

In the structure that the moving housing 22 is mounted to be rotatable, with a rotary axis as a center, with respect to the fixed housing 21, the actuation part 63 of the specimen vessel pressing release means can be constructed in such a way that a plate-shaped member having a preset length so that its one end is mounted to be rotatable, with a rotary axis as a center, with respect to the moving housing 22 and a remaining end is mounted to be guidable at least in a horizontal direction through a guide member (not shown) provided to the fixed housing 21 is used, and when the moving housing 22 is rotated, with the rotary axis as the center, with respect to the fixed housing 21, a part of the plate-shaped member pressing the end $62b^2$ opposite to the pressing part $62b^1$ of the release lever is displaced along a longitudinal direction.

In the box-type microscope apparatus of the first embodiment constructed as mentioned above, the replacement of the specimen vessel is made as described below.

The electric stage 12 is moved to a preset reference position where the replacement of the specimen vessel can be made. Subsequently, the moving housing 22 is moved in a direction of the opened state. Then, the actuation part 63 of the specimen vessel pressing release means is moved in the direction of an arrow A (FIG. 6). When the moving housing 22 is move by a preset amount, the actuation part 63 of the specimen vessel pressing release means presses the end $62b^2$ of the release lever that is the specimen vessel pressing release means 62 and rotates the lever body $62b$, with the shaft $62a$ as a center, in the direction of an arrow B against a tensile force of the spring $62c$. When the moving housing 22 reaches the position of the opened state, the release lever 62 presses the engagement part 61 of the clamp lever 52 that is the specimen vessel pressing means, through the pressing part $62b^1$, and rotates the lever body $52b$, with the shaft $52a$ as a center, in the direction of an arrow C (in a direction opposite to a direction in which the specimen vessel 40 is pressed) against a tensile force of the spring $52c$. At this time, the pressing part $52b^1$ separates from the position where the corner $40c^1$ of the specimen vessel 40 is pressed. Whereby, loading and unloading of the specimen vessel 40 onto and from a place surrounded by the frame-shaped member 51 on the electric stage 12 become possible. The specimen vessel 40 is taken out by holding the pair of side surfaces $40b$ and $40b'$ of the specimen vessel 40 through the notches $51d$ and $51d'$.

Subsequently, another specimen vessel 40 is loaded onto the place surrounded by the frame-shaped member 51. After loading of the specimen vessel 40, the moving housing 22 is moved in a direction of the closed state. At this time, the actuation part 63 of the specimen vessel pressing release means is moved in a direction opposite to that of the arrow A. Whereby, a pressing of the actuation part 63 of the specimen vessel pressing release means on the end $62b^2$ of the release lever that is the specimen vessel pressing release means 62 is gradually reduced and then is released. When the pressing of the actuation part 63 of the specimen vessel pressing release means on the end $62b^2$ of the release lever is released, the tensile force of the spring 62c is exerted and the lever body 62b is rotated on the shaft 62a in a direction opposite to that of the arrow B. At this time, the pressing on the engagement part 61 of the clamp lever 52 that is the specimen vessel pressing means, through the pressing part $62b^1$ of the release lever 62, is released. Whereby, the tensile force of the spring 52c is exerted and the lever body 52b is rotated, with the shaft 52a as a center, in a direction opposite to that of the arrow C (in the direction of an arrow D). At this time, the pressing part $52b^1$ presses the corner $40c^1$ of the specimen vessel 40. Whereby, the specimen vessel 40 is moved toward the X-direction bumping part 51a and the Y-direction bumping part 51b of the frame-shaped member 51, and the side surfaces 40a and 40b abut on the bumping parts 51a and 51b, respectively. In this state, the specimen vessel 40 on the electric stage 12 is fixed to a constant position. After the specimen vessel 40 is fixed to the electric stage 12, the electric stage 12 is moved by a preset amount from the preset reference position and thereby the observation and/or measurement are carried out. When the replacement of the specimen vessel 40 is made, the procedure outlined above is repeated.

According to the box-type microscope apparatus of the first embodiment, therefore, the specimen vessel 40 can be always fixed to a constant position by a simple operation, and the positional adjustment of the specimen vessel 40 becomes unnecessary. In addition, the specimen vessel 40 mounted to the electric stage 12 can be always located at a constant position. As a result, the electric stage 12 is only moved by a constant amount, for example, with a position detected by a position sensor of the electric stage 12 as a reference, and thereby a desired part in the specimen vessel 40 can be located at a correct observation and/or measurement position (namely, a preset position on the optical axis connecting the illumination optical system with the image forming optical system).

Figure 7:
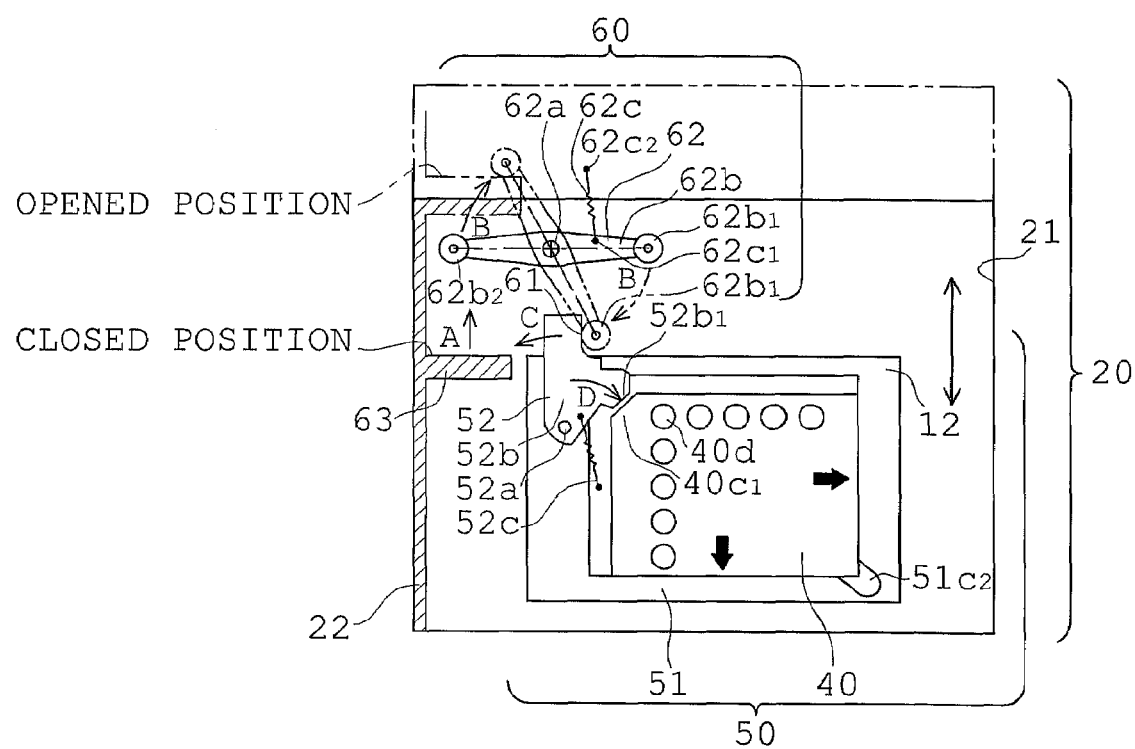
FIG. 7 is an explanatory view showing one modified example of an electric stage.

Also, each of the examples of FIGS. 5 and 6 is constructed so that the frame-shaped member constituting the bumping part 51 is surrounded by practical four sides, excluding surroundings of the actuation part of the specimen vessel pressing means 52, and the notches 51d and 51d' are provided to take out the specimen vessel 40 while holding the pair of side surfaces 40b and 40b' of the specimen vessel 40. However, as shown in the modified example of FIG. 7, the electric stage 12 may be constructed so that the frame-shaped member is surrounded by three sides and the notches 51d and 51d' are not provided. In this case, it becomes easy to load and unload the specimen vessel 40 with respect to the electric stage 12 through a part not surrounded. In each of the examples of FIGS. 5 and 6, the frame-shaped member constituting the bumping part 51 is provided with the notches $51c^1$ and $51c^3$ in addition to the notch $51c^2$, but as shown in FIG. 7, the notches $51c^1$ and $51c^3$ need not necessarily be provided.

In the box-type microscope apparatus of the first embodiment, the specimen vessel pressing release means 62 is provided to the fixed housing 21, but it may be provided to the electric stage 12 if there is space for placement. In the case where the specimen vessel pressing release means 62 is provided to the electric stage 12, the relative positions of the specimen vessel pressing means 52 and the specimen vessel pressing release means 62 become constant, regardless of the amount of movement of the electric stage 12. Consequently, operation accuracy of the pressing release of the specimen vessel pressing release means 62 relative to the specimen vessel pressing means 52 is improved.

Also, the specimen vessel 40 shown in each of FIGS. 4-7 substantially satisfies a preset standard (the SBS standard), but partially, the corner $40c^1$ is chamfered so that the specimen vessel 40 is easily pressed through the specimen vessel pressing means 52. For the shape of the chamfer of the corner $40c^1$ of the specimen vessel 40, an arbitrarily designed face (for example, a curved face or flat face) can be used. In addition, the specimen vessel 40 in which the chamfer of the corner $40c^1$ is not applied may be used. Thus, in the box-type microscope apparatus of the first embodiment, it is desirable that even when the specimen vessel 40 is replaced with a specimen vessel of the corner $40c^1$ of a different shape, the pressing part $52b^1$ of the specimen vessel pressing means 52 is designed to have a shape, size, and moving stroke such that the side surfaces of the specimen vessel are made to abut on the bumping parts 51a and 51b and the specimen vessel can be fixed.

Also, although the box-type microscope apparatus of the first embodiment is constructed so that the moving housing is manually opened and closed, it may be constructed so that the moving housing can be automatically opened and closed through a driving means. The box-type microscope apparatus of the first embodiment is further constructed so that the microscope includes the reflecting illumination optical system, but it is also applicable to the structure in which the reflecting illumination optical system is not included.

Subsequently, more specific embodiments of the box-type microscope apparatus of the present invention will be explained with reference to the drawings.

Specific Embodiment 1

Figure 8:
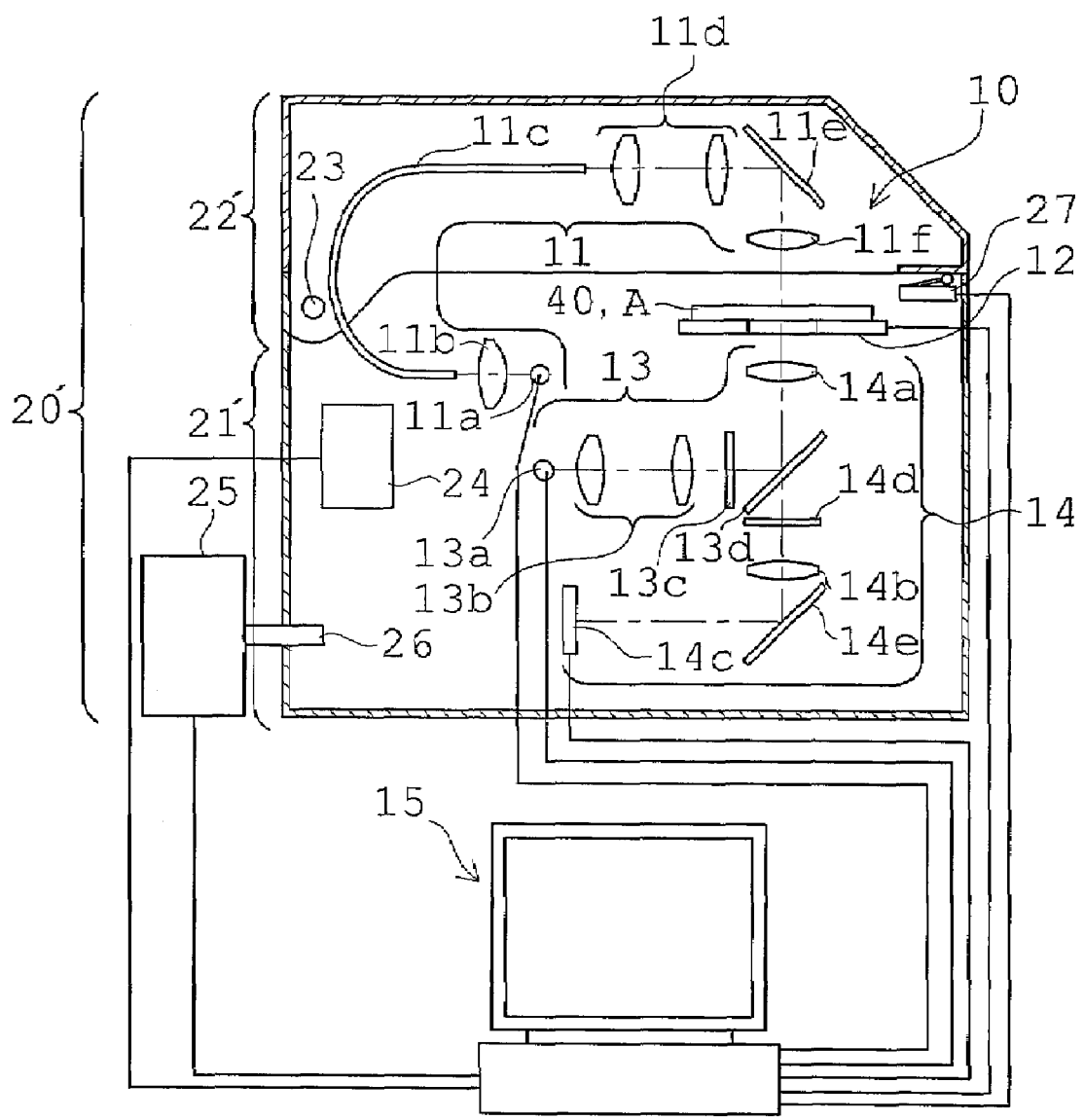
FIG. 8 is an explanatory view showing a schematic general structure of the box-type microscope apparatus according to the first embodiment.
Figure 9:
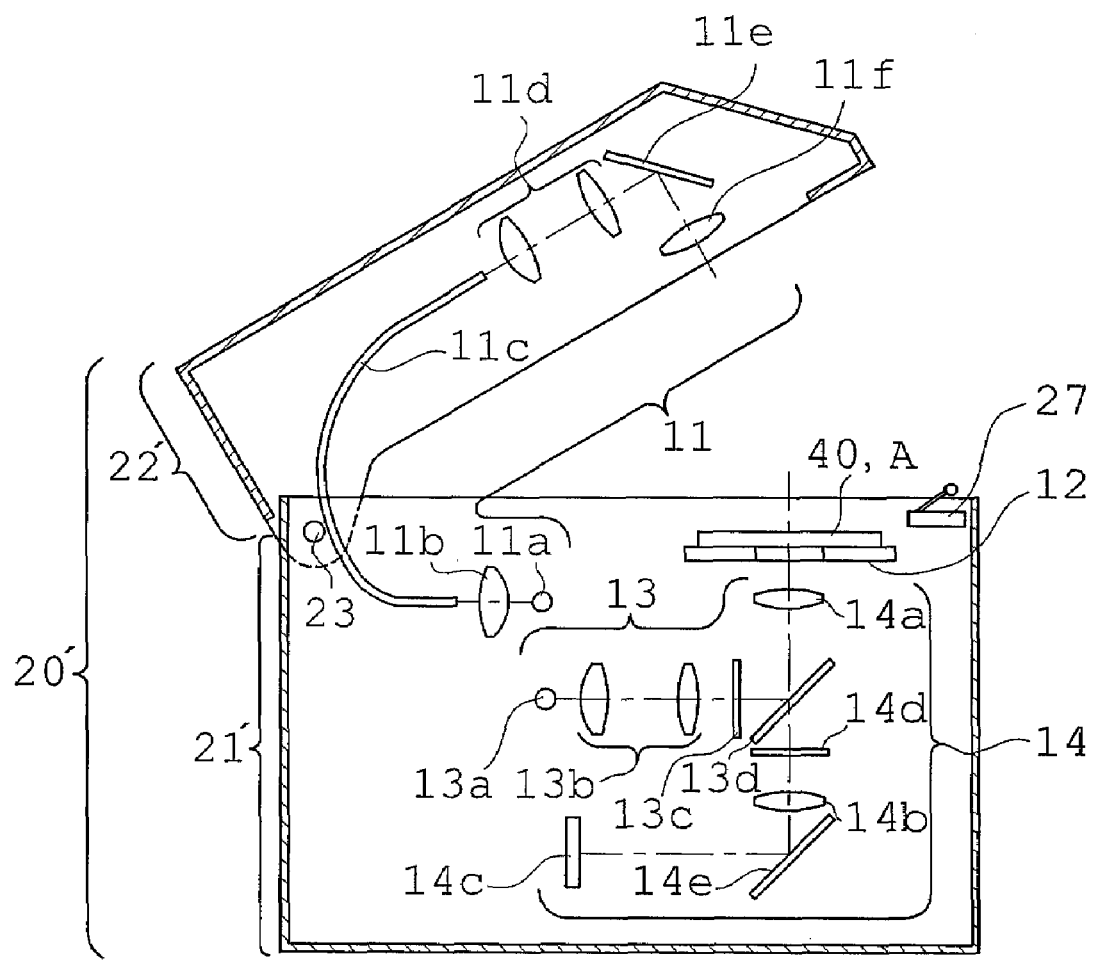
FIG. 9 is an explanatory view showing a state where the moving housing is opened in the box-type microscope apparatus of FIG. 8.
Figure 10A:
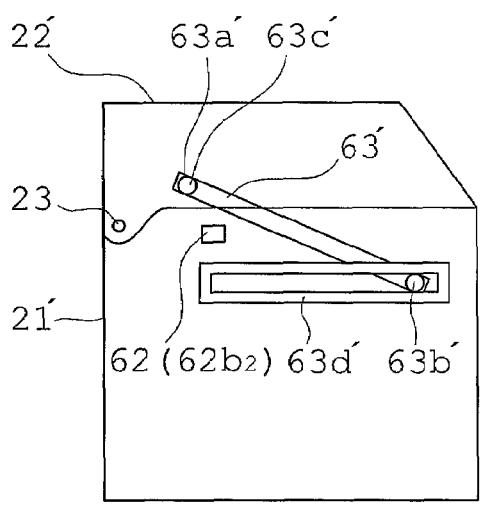
FIGS. 10A, 10B, 10C, and 10D are explanatory views of essential parts of the structure of an actuation part of a specimen vessel pressing release means in the box-type microscope apparatus of FIG. 8, which are a side view conceptually showing a state of the actuation part where the moving housing is closed; a side view conceptually showing a state of the actuation part where the moving housing is opened; a partially longitudinal sectional view of FIG. 1 OA, showing the structure of a mounting portion of the actuation part to the fixed housing; and a partially longitudinal sectional view of FIG. 10A, showing the structure of a mounting portion of the actuation part to the moving housing, respectively.

FIG. 8 is an explanatory view showing a schematic general structure of the box-type microscope apparatus according to Specific Embodiment 1 of the present invention, and FIG. 9 is an explanatory view showing a state where the moving housing is opened in the box-type microscope apparatus of FIG. 8. FIGS. 10A, 10B, 10C, and 10D are explanatory views of essential parts of the structure of an actuation part of a specimen vessel pressing release means in the box-type microscope apparatus of FIG. 8, which are a side view conceptually showing a state of the actuation part where the moving housing is closed; a side view conceptually showing a state of the actuation part where the moving housing is opened; a partially longitudinal sectional view of FIG. 10A, showing the structure of a mounting portion of the actuation part to the fixed housing; and a partially longitudinal sectional view of FIG. 10A, showing the structure of a mounting portion of the actuation part to the moving housing, respectively. Also, like numerals are used for like members with respect to the first embodiment.

The box-type microscope apparatus of Specific Embodiment 1 comprises an inverted microscope 10 and a housing 20' incorporating the inverted microscope 10.

The inverted microscope 10 includes the transmitting illumination optical system 11, the electric stage 12, the reflecting illumination optical system 13, the image forming optical system 14, and a control section 15. The transmitting illumination optical system 11 has a halogen lamp 11*a*, a coupling lens 11*b* condensing white light emitted from the halogen lamp 11*a*, an optical fiber 11*c* making the white light condensed by the coupling lens 11*b* incident on its one end, a collector lens lid collecting the white light propagated by the optical fiber 11*c* and emerging from the other end, a mirror lie reflecting the white light collected by the collector lens 11*d* to direct the white light in a vertical downward direction, and a condenser lens 11*f* condensing the white light reflected by the mirror 11*e*. The optical fiber 11*c* is the flexible one, such as a liquid fiber, which can be freely bent. The transmitting illumination optical system 11 is constructed so that the specimen in the specimen vessel 40, for example, consisting of the microplate, placed on the electric stage 12 is irradiated with the white light in a vertical direction from above.

The electric stage 12 is constructed so that a specimen A can be placed thereon. The electric stage 12 has a specimen positioning means (omitted from FIG. 8) constructed in the. same way as the specimen vessel positioning means 50 shown in FIGS. 4 and 6 of the first embodiment so that the specimen A can be fixed through the specimen positioning means. The electric stage 12 is also constructed to be slidable in the X and Y directions so that a desired part in the specimen vessel 40 (for example, a desired well in the microplate) can be moved to an observation position through a driving means (not shown) by the control of a computer constituting the control section 15.

The reflecting illumination optical system 13 is placed below the electric stage 12 and includes a xenon lamp 13*a*, a collector lens 13*b* collecting light emitted from the xenon lamp 13*a*, a wavelength selective filter 13*c* selectively transmitting excitation light of particular wavelength, a dichroic mirror 13*d* reflecting the excitation light transmitted through the wavelength selective filter 13*c*, and the objective lens 14*a* condensing the excitation light reflected by the dichroic mirror 13*d* to irradiate the specimen A with the excitation light. The reflecting illumination optical system 13 is constructed so that the specimen A in the specimen vessel 40 placed on the electric stage 40 is irradiated with the excitation light in a vertical direction from below.

The image forming optical system 14 has the objective lens 14*a* and the dichroic mirror 13*d* of the reflecting illumination optical system 13 in common and includes a wavelength selective filter 14*d* transmitting fluorescent light emanating from the specimen A, condensed by the objective lens 14*a*, and transmitted through the dichroic mirror 13*d*; the image forming lens 14*b* condensing the fluorescent light transmitted through the wavelength selective filter 14*d*; and the CCD 14*c* camera detecting the fluorescent light condensed by the image forming lens 14*b*. In FIG. 8, reference numeral 14*e* represents a mirror.

The housing 20' is constructed with a fixed housing 21' on the lower side and a moving housing 22' on the upper side. The fixed housing 21' is fixedly placed in a state where optical elements arranged below the electric stage 12, including the electric stage 12, are held. The moving housing 22' is rotatably supported by the fixed housing 21' so as to bring about an opened state shown in FIG. 9 from a closed state in FIG. 8 by rotating on a rotary axis 23 through a rotation mechanism, not shown, like a bearing while holding optical elements (from the other end of the optical fiber 11*c* in the transmitting illumination optical system 11 to the condenser lens 11*f*) arranged above the electric stage 12. The hosing 20' is constructed so that the moving housing 22' is rotated in a direction of the opened state by a preset amount and thereby the fixed housing 21' is opened to make the specimen vessel 40 placed on the electric stage 12 replaceable, while it is rotated in a direction of the closed state to abut on the fixed housing 21' and thereby the inverted microscope 10 is sealed and light-blocked in corporation with the fixed housing 21' and the optical axis of the transmitting illumination optical system 11 is aligned with that of the image forming optical system 14.

Inside the housing 20', a temperature controller 24 for controlling the temperature of the interior of the hosing 20' is placed. A carbon dioxide supply device 25 supplying carbon dioxide into the housing 20' is connected to the housing 20' through a duct 26. In addition, between the fixed housing 21' and the moving housing 22', a sensor 27, such as a microswitch or photointerrupter, for detecting opened and closed states between both these housings is provided. The control section 15 is connected to the electric sage 12, the xenon lamp 13*a*, the halogen lamp 11*a*, the CCD camera 14*c*, the temperature controller 24, the carbon dioxide supply device 25, and the sensor 27.

Figure 10B:
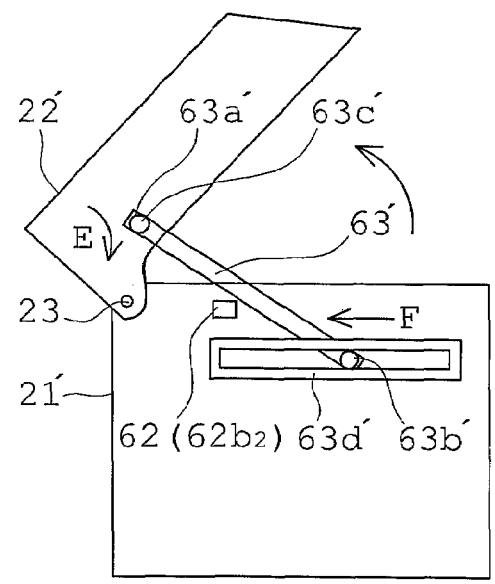
Figure 10C:
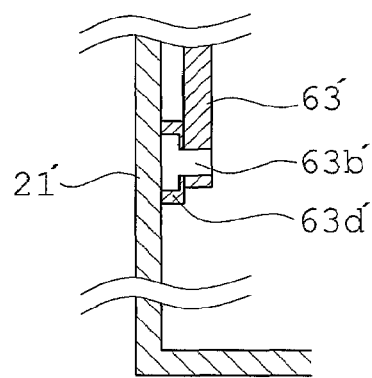
Figure 10D:
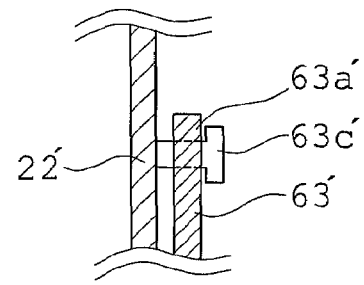

The box-type microscope apparatus of Specific Embodiment 1 includes a positioning release means. The positioning release means has the engagement part, the specimen vessel pressing release means, and the actuation part of the specimen vessel pressing release means (not shown in FIG. 8). The engagement part and the specimen vessel pressing release means are constructed in the same way as the engagement part 61 and the specimen vessel pressing release means 62 shown in FIG. 6. The actuation part of the specimen vessel pressing release means, as illustrated in FIGS. 10A and 10B, is constructed with a plate-shaped member 63' having a preset length whose one end 63*a'* is mounted to be rotatable on a rotary axis 63*c'* with respect to the moving housing 22' and whose remaining end 63*b'* is mounted to be guidable at least in a horizontal direction through a guide member 63*d'* provided to the fixed housing 21' so that when the moving housing 22' is rotated on the rotary axis 23 with respect to the fixed housing 21', a part of the plate-shaped member 63' pressing the end 62*b*$^2$ opposite to the pressing part 62*b*$^1$ of the release lever is displaced along a longitudinal direction.

The actuation part 63' of the specimen vessel pressing release means presses the specimen vessel pressing release means 62 and thereby the pressing of the specimen vessel pressing means 52 on the specimen vessel 40 is released through the specimen vessel pressing release means 62 shown in FIG. 6 so that when the moving housing 22' is located at the position of the opened state with respect to the fixed housing 21', a release from the pressing on the specimen vessel 40 applied by the specimen vessel pressing means 52 is completed through the specimen vessel pressing release means 62. Other features are nearly the same as in the box-type microscope apparatus of the first embodiment.

In order to use the box-type microscope apparatus of Specific Embodiment 1 constructed as mentioned above to curry out the observation of the specimen, the electric stage 12 is first moved to a preset reference position where the replacement of the specimen vessel becomes possible. Subsequently, the moving housing 22' is rotated in the direction of the opened state. At this time, as shown in FIG. 10B, the one end 63*a'* of the plate-shaped member constituting the actuation part 63' of the specimen vessel pressing release means is rotated on the rotary axis 63*c'* in the direction of an arrow E with respect to the moving housing 22' and the remaining end 63*b'* is moved in the direction of an arrow F through the guide member 63*d'* provided to the fixed housing 21'. When the moving housing 22' is rotated. in the direction of the opened state by a preset amount, the actuation part 63' of the specimen vessel pressing release means presses the end 62*b*$^2$ of the release lever that is the specimen vessel pressing release means while shifting the position of the plate-shaped member pressing the end $62b^2$ opposite to the pressing part $62b^2$ of the release lever along the longitudinal direction and as shown in FIG. 6, rotates the lever body 62 on the shaft $62a$ in the direction of the arrow B against the tensile force of the spring $62c$. When the moving housing 22' reaches the position of a fully opened state, the release lever 62 presses the engagement part 61 of the clamp lever 52 that is the specimen vessel pressing means, through the pressing part $62b^2$ and rotates the lever body $52b$ on the shaft $52a$ in the direction of the arrow C (in a direction opposite to that of the pressing on the specimen vessel 40) against the tensile force of the spring $52c$. Whereupon, the pressing part $52b^1$ separates from the position where it presses the corner $40c^1$ of the specimen vessel 40. Whereby, the loading and unloading of the specimen vessel 40 onto and from the place surrounded by the frame-shaped member 51 on the electric stage 12 become possible.

The housing 22', as shown in FIG. 9, is held in a lifted state by a clamp mechanism, not shown. At this time, the transmitting illumination optical system 11 arranged above the electric stage 12 is lifted together with the moving housing 22', and the electric stage 12 is exposed in a state where a wide space is occupied above the electric stage 12. In this state, when the specimen vessel 40 to be replaced that has been already observed is placed on the electric stage 12, an operator holds the pair of side surfaces $40b$ and $40b'$ of the specimen vessel 40 through the notches $51d$ and $51d'$ shown in FIG. 6 to take out the specimen vessel 40. The operator then places the specimen vessel 40 on the electric stage 12 in a state where the specimen A, such as a medium cell labeled by fluorescence, is incorporated in the specimen vessel 40, such as a microplate.

Also, in the above description, after the electric stage 12 is moved to the preset reference position where the replacement of the specimen vessel 40 becomes possible, the moving housing 22' is moved in the direction of the opened stated. However, since the moving housing 22' is opened with respect to the fixed housing 21' and thereby the opened state is detected by the sensor 27, the control section 15 may be designed so that, in accordance with this detection signal, the electric stage 12 is moved to the preset reference position where the replacement of the specimen vessel becomes possible.

Subsequently, after the operator places the specimen vessel 40 incorporating the specimen A on the electric stage 12, the moving housing 22' is moved in the direction of the closed state. In this case, the one end $63a'$ of the plate-shaped member constituting the actuation part 63' of the specimen vessel pressing release means shown in FIG. 10A is rotated on the rotary axis $63c'$ in the direction opposite to that of the arrow E with respect to the fixed housing 21', and the remaining end $63b'$ is guided along the guide member $63d'$ provided to the fixed housing 21' and is moved in the direction opposite to that of the arrow F. When the moving housing 22' is moved in the direction of the closed state by a preset amount, the actuation part 63' of the specimen vessel pressing release means is such as to displace the part of the plate-shape member pressing the end $62b^2$ opposite to the pressing part $62b^1$ of the release lever along a longitudinal direction. The pressing of the actuation part 63' of the specimen vessel pressing release means on the end $62b^2$ of the release lever that is the specimen vessel pressing release means 62 is gradually reduced and then is released. When the pressing of the actuation part 63' of the specimen vessel pressing release means on the end. $62b^2$ of the release lever is released, the tensile force of the spring $62c$ shown in FIG. 6 is exerted and the lever body $62b$ is rotated on the shaft $62a$ in a direction opposite to that of the arrow B. At this time, the pressing on the engagement part 61 of the clamp lever 52 that is the specimen vessel pressing means, through the pressing part $62b^1$ of the release lever 62, is released. Whereby, the tensile force of the spring $52c$ is exerted and the lever body $52b$ is rotated on the shaft $52a$ in a direction opposite to that of the arrow C (in the direction of the arrow D). At this time, the pressing part $52b$, presses the corner $40c^1$ of the specimen vessel 40. Whereby, the specimen vessel 40 is moved toward the X-direction bumping part $51a$ and the Y-direction bumping part $51b$ of the frame-shaped member 51, and the specimen vessel 40 is fixed to a constant position with respect to the electric stage 12 in a state where the side surfaces $40a$ and $40b$ abut on the bumping parts $51a$ and $51b$, respectively.

When the moving housing 22' is closed, the sensor 27 outputs the detection signal of the closed state. In this state, the transmitting illumination optical system 11 provided to the moving housing 22' is located at the position where the optical axis of the condenser lens $11f$ is aligned with that of the objective lens $14a$. The control section 15 receiving the detection signal of the closed state from the sensor 27 drives and controls the electric stage 12 to a preset position in accordance with a preset program. The control section 15 actuates the halogen lamp $11a$ or the xenon lamp $13a$, and then the CCD camera $14c$, thereby automatically starting the image acquirement of the specimen A. The driving control of the electric stage 12, for example, may be such as to automatically pick up in turn the image of each well of the microplate 40 incorporating the specimen A, or to control a focus section, not shown, of the objective lens $14a$ for focusing operation control. Image information acquired by image pickup through the CCD camera $14c$ is displayed as a fluorescent image on a monitor by processing the image in the control section 15.

Also, the control section 15 is capable of controlling turning on and off of the halogen lamp $11a$ or the xenon lamp $13a$ by receiving the detection signal from the sensor 27. Specifically, when it is detected that the operator opens the moving housing 22', the halogen lamp $11a$ or the xenon lamp $13a$ is turned off, while it is detected that the moving housing 22' is closed, the lamp is turned on. Similarly, for the temperature controller 24 and the carbon dioxide supply device 25, the control section 15 is capable of making control in accordance with the detection signal of the sensor 27.

According to the box-type microscope apparatus of Specific Embodiment 1, the specimen vessel 40 can be always fixed to a constant position by a simple operation, and the positional adjustment of the specimen vessel 40 becomes unnecessary. In addition, the specimen vessel 40 mounted to the electric stage 12 can be always located at a constant position. As a result, the electric stage 12 is only moved by a constant amount, for example, with a position detected by a position sensor of the electric stage 12 as a reference, and thereby a desired part in the specimen vessel 40 can be located at a correct observation and/or measurement position (namely, a preset position on the optical axis connecting the illumination optical system with the image forming optical system).

Specific Embodiment 2

Figure 11:
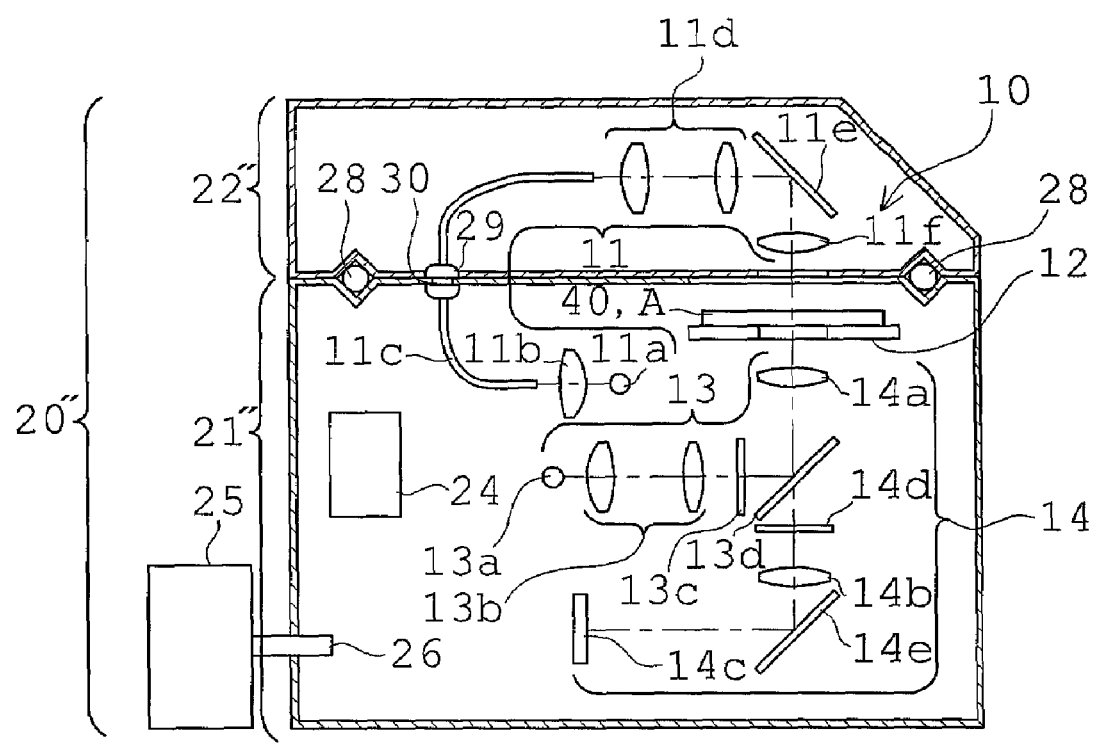
FIG. 11 is an explanatory view showing a schematic general structure of the box-type microscope apparatus according to a second embodiment in the present invention.
Figure 12A:
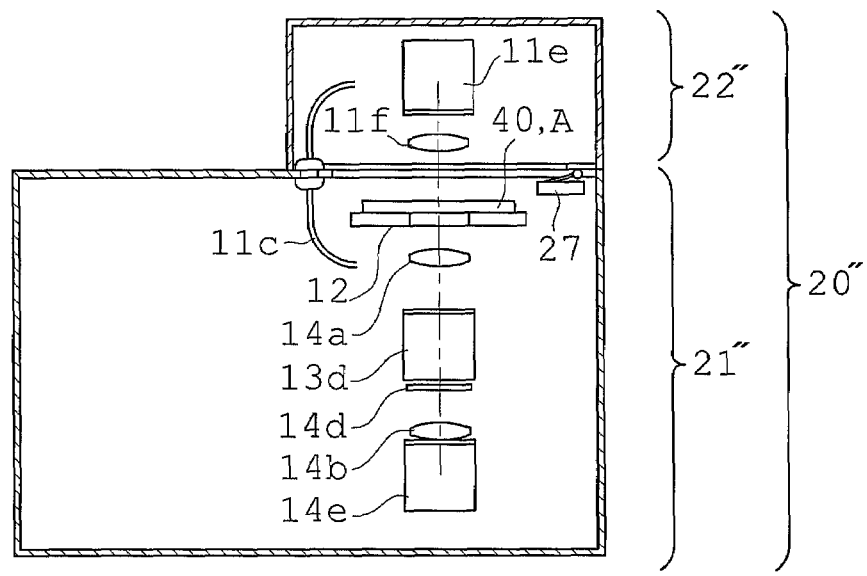
FIGS. 12A and 12B are explanatory views showing opened and closed states of the moving housing in the box-type microscope apparatus of FIG. 11, which are a state where the moving housing is closed and a state where it is opened, respectively.
Figure 12B:
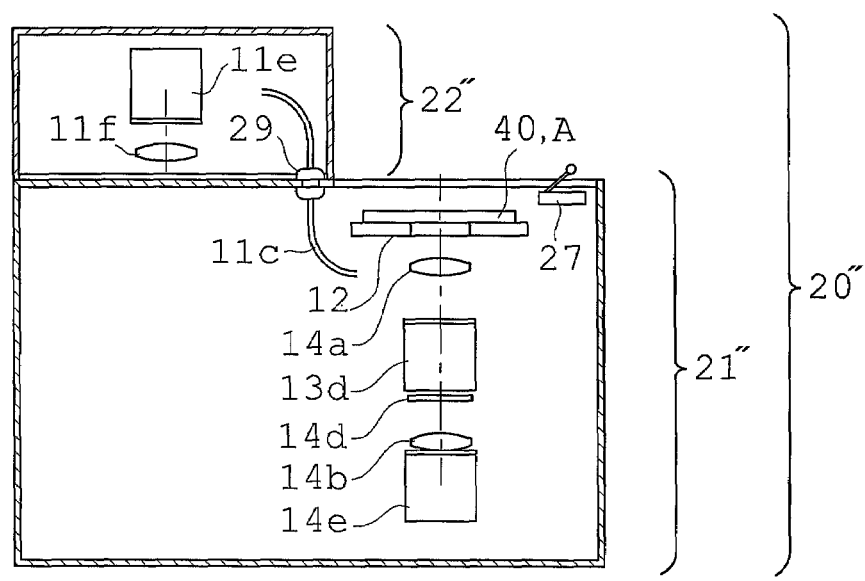
Figure 13A:
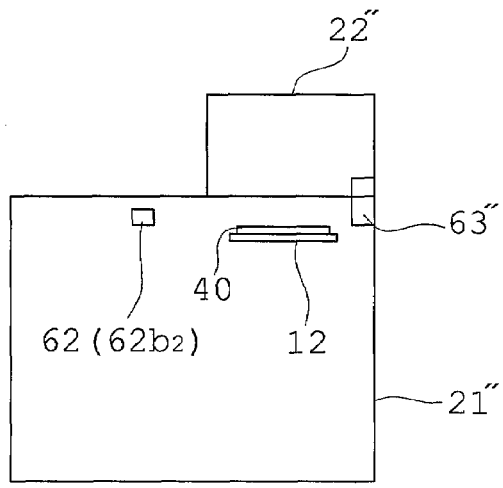
FIGS. 13A, 13B, and 13C are explanatory views of essential parts of the structure of the actuation part of the specimen vessel pressing release means in the box-type microscope apparatus of FIG. 11, which are a side view conceptually showing a state of the actuation part where the moving housing is closed; a side view conceptually showing a state of the actuation part where the moving housing is opened; and a partially longitudinal sectional view of FIG. 13A in the actuation part, respectively.
Figure 13B:
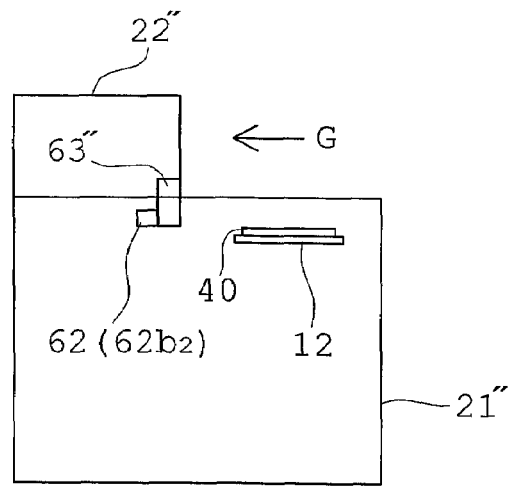
Figure 13C:
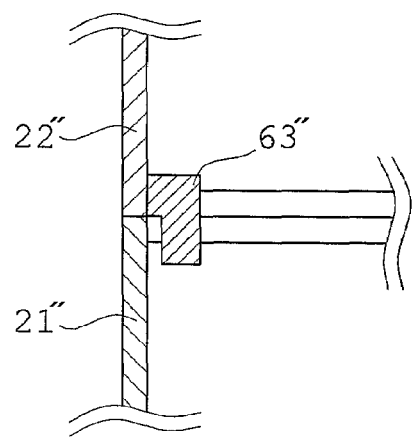

FIG. 11 is an explanatory view showing a schematic general structure of the box-type microscope apparatus according to Specific Embodiment 2 in the present invention. FIGS. 12A and 12B are explanatory views showing opened and closed states of the moving housing in the box-type microscope apparatus of FIG. 11, which are a state where the moving housing is closed and a state where it is opened, respectively. FIGS. 13A, 13B, and 13C are explanatory views of essential parts of the structure of the actuation part of the specimen vessel pressing release means in the box-type microscope apparatus of FIG. 11, which are a side view conceptually showing a state of the actuation part where the moving housing is closed; a side view conceptually showing a state of the actuation part where the moving housing is opened; and a partially longitudinal sectional view of FIG. 13A in the actuation part, respectively.

The box-type microscope apparatus of Specific Embodiment 2 is constructed in almost the same way as Specific Embodiment 1 with the exception of the structures of a housing 20" and a positioning release means. The housing 20" is provided with a moving housing 22" that can be moved in a horizontal direction by direct-acting guides 28, on a fixed housing 21" placed on the lower side. Between the fixed housing 21" and the moving housing 22", a click mechanism, not shown, is provided so that the moving housing 22" is able to keep the opened state and the closed state with respect to the fixed housing 21". The optical fiber 11c is placed to act as a bridge between the fixed housing 21" and the moving housing 22". An intermediate position of the optical fiber 11c in a longitudinal direction is secured by a bush 29 passing through the ceiling surface of the fixed housing 21". The wall of the moving housing 22" corresponding to the bush 29 is provided with a slot 30 keeping the moving housing 22" so that the moving housing 22" does not interfere with the bush 29 from the opened state to the closed state.

The poisoning release means includes the engagement part, the specimen vessel pressing release means, and the actuation part of the specimen vessel pressing release means (not shown in FIG. 11). The engagement part and the specimen vessel pressing release means are constructed in the same way as the engagement part 61 and the specimen vessel pressing release means 62 shown in FIG. 6. An actuation part 63" of the specimen vessel pressing release means, as illustrated in FIGS. 13A-13C, is constructed with a projection provided to the moving housing 22". The actuation part 63" of the specimen vessel pressing release means releases the pressing on the specimen vessel 40 applied by the specimen vessel pressing means 52 through the specimen vessel pressing release means 62 shown in FIG. 6 by pressing the specimen vessel pressing release means 62 so that when the moving housing 22" is located at the position of the opened state with respect to the fixed housing 21", a release from the pressing on the specimen vessel 40 applied by the specimen vessel pressing means 52 is completed through the specimen vessel pressing release means 62. Other features are almost the same as in the box-type microscope apparatus of the first embodiment or Specific Embodiment 1.

In order to use the box-type microscope apparatus of Specific Embodiment 2 constructed as mentioned above to curry out the observation of the specimen, the electric stage 12 is first moved to a preset reference position where the replacement of the specimen vessel becomes possible. Subsequently, the moving housing 22" is moved in the direction of the opened state. At this time, as shown in FIG. 13B, the projection constituting the actuation part 63" of the specimen vessel pressing release means is moved integrally with the moving housing 22" in the direction of an arrow G along the direct-acting guides 28. When the moving housing 22" is moved in the direction of the opened state by a preset amount, the actuating part 63" of the specimen vessel pressing release means presses the end $62b^2$ of the release lever that is the specimen vessel pressing release means and as shown in FIG. 6, rotates the lever body 62b on the shaft 62a in the direction of the arrow B against the tensile force of the spring 62c. When the moving housing 22" reaches the position of the opened state, the release lever 62 presses the engagement part 61 of the clamp lever 52 that is the specimen vessel pressing means, through the pressing part $62b^1$ and rotates the lever body 52b, with the shaft 52a as a center, in the direction of the arrow C (in the direction opposite to the direction in which the specimen vessel 40 is pressed) against a tensile force of the spring 52c. At this time, the pressing part $52b^1$ separates from the position where the corner $40c^1$ of the specimen vessel 40 is pressed. Whereby, the loading and unloading of the specimen vessel 40 onto and from the place surrounded by the frame-shaped member 51 on the electric stage 12 become possible.

At this time, the transmitting illumination optical system 11 is removed together with the moving housing 22" from above the stage 12. In this state, when the specimen vessel 40 to be replaced that has been already observed is placed on the stage 12, an operator holds the pair of side surfaces 40b and 40b' of the specimen vessel 40 through the notches 51d and 51d' shown in FIG. 6 to take out the specimen vessel 40. The operator then places the specimen vessel 40 on the electric stage 12 in a state where the specimen A, such as a medium cell labeled by fluorescence, is incorporated in the specimen vessel 40, such as a microplate. After the operator places the specimen vessel 40 incorporating the specimen A on the electric stage 12, the moving housing 22" is moved in the direction of the closed state. In this case, the projection constituting the actuating part 63" of the specimen vessel pressing release means shown in FIG. 13B is moved integrally with the moving housing 22" in the direction opposite to that of the arrow G along the direct-acting guides 28.

When the moving housing 22" is moved in the direction of the closed state by a preset amount, the pressing of the actuation part 63" of the specimen vessel pressing release means on the end $62b^2$ of the release lever that is the specimen vessel pressing release means 62 is gradually reduced and then is released. When the pressing of the actuation part 63" of the specimen vessel pressing release means on the end $62b^2$ of the release lever is released, the tensile force of the spring 62c shown in FIG. 6 is exerted and the lever body 62b is rotated on the shaft 62a in a direction opposite to that of the arrow B. At this time, the pressing on the engagement part 61 of the clamp lever 52 that is the specimen vessel pressing means, through the pressing part $62b^1$ of the release lever 62, is released. Whereby, the tensile force of the spring 52c is exerted and the lever body 52b is rotated, with the shaft 52a as a center, in a direction opposite to that of the arrow C (in the direction of an arrow D). At this time, the pressing part $52b^1$ presses the corner $40c^1$ of the specimen vessel 40.

Whereby, the specimen vessel 40 is moved toward the X-direction bumping part 51a and the Y-direction bumping part 51b of the frame-shaped member 51, and the side surfaces 40a and 40b abut on the bumping parts 51a and 51b, respectively. In this state, the specimen vessel 40 on the electric stage 12 is fixed to a constant position. When the moving housing 22" is closed, the sensor 27 outputs the detection signal of the closed state. In this state, the transmitting illumination optical system 11 provided to the moving housing 22" is located at the position where the optical axis of the condenser lens 11f is aligned with that of the objective lens 14a. Other functions are almost the same as in the box-type microscope apparatus of the first embodiment or Specific Embodiment 1.

In the box-type microscope apparatus of Specific Embodiment 2 as well, like the box-type microscope apparatus of Specific Embodiment 1, the specimen vessel 40 can be always fixed to a constant position by a simple operation, and the positional adjustment of the specimen vessel 40 becomes unnecessary. In addition, the specimen vessel 40 mounted to the electric stage 12 can be always located at a constant position. As a result, the electric stage 12 is only moved by a constant amount, for example, with a position detected by a position sensor of the electric stage 12 as a reference, and thereby a desired part in the specimen vessel 40 can be located at a correct observation and/or measurement position (namely, a preset position on the optical axis connecting the illumination optical system with the image forming optical system).

Specific Embodiment 3

Figure 14:
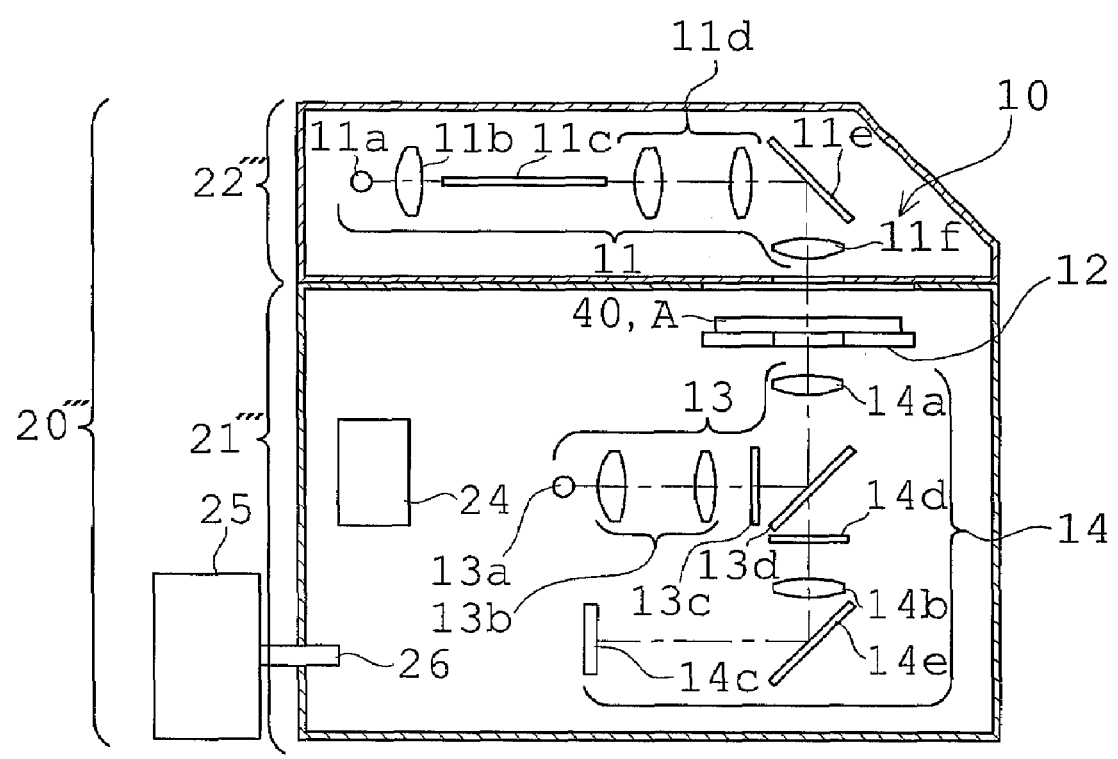
FIG. 14 is an explanatory view showing a schematic general structure of the box-type microscope apparatus according to a third embodiment in the present invention.
Figure 15A:
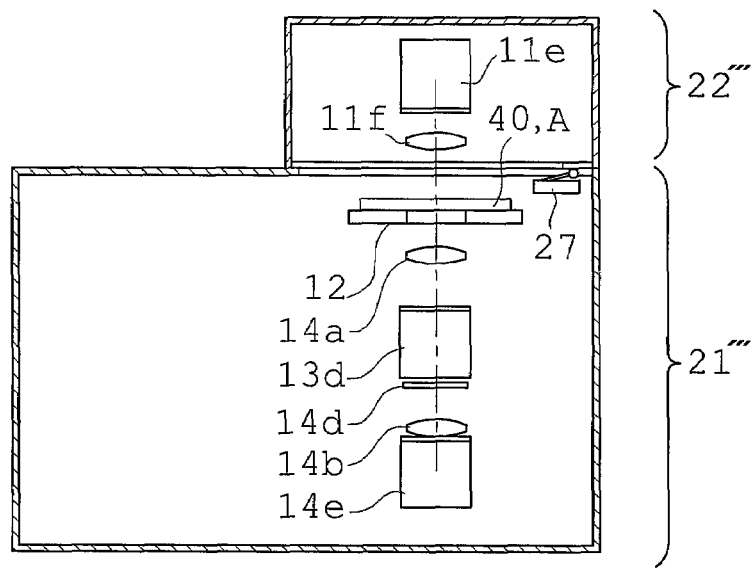
FIGS. 15A and 15B are explanatory views showing opened and closed states of the moving housing in the box-type microscope apparatus of FIG. 14, which are a state where the moving housing is closed and a state where it is opened, respectively.
Figure 15B:
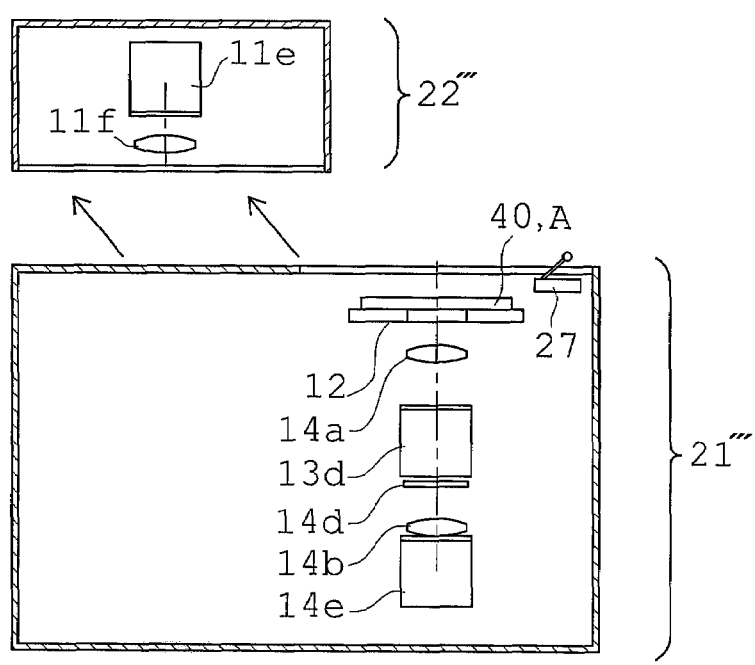
Figure 17A:
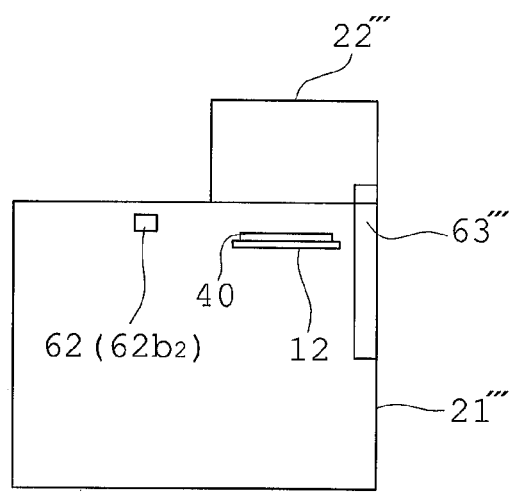
FIGS. 17A, 17B, and 17C are explanatory views of essential parts of the structure of the actuation part of the specimen vessel pressing release means in the box-type microscope apparatus of FIG. 14, which are a side view conceptually showing a state of the actuation part where the moving housing is closed; a side view conceptually showing a state of the actuation part where the moving housing is opened; and a partially longitudinal sectional view of FIG. 17A in the actuation part, respectively.
Figure 17B:
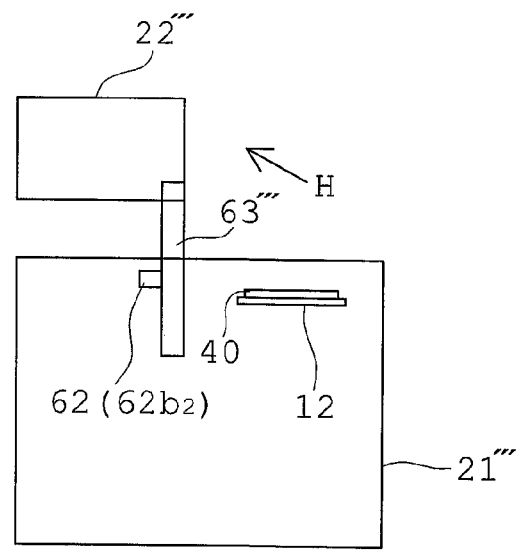
Figure 17C:
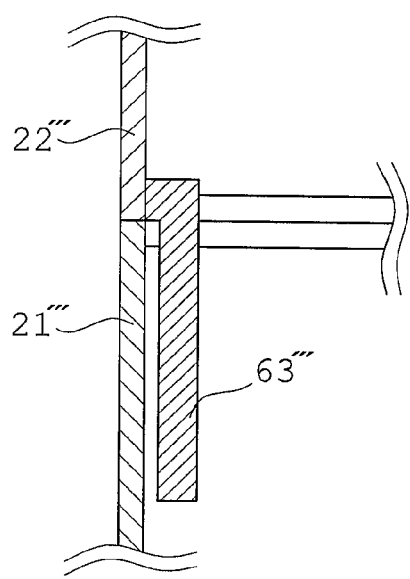

FIG. 14 is an explanatory view showing a schematic general structure of the box-type microscope apparatus according to Specific Embodiment 3 in the present invention and FIGS. 15A and 15B are explanatory views showing opened and closed states of the moving housing in the box-type microscope apparatus of FIGS. 13A-13C, which are a state where the moving housing is closed and a state where it is opened, respectively. FIGS. 16A and 16B are explanatory views showing a movement mechanism of the moving housing in the box-type microscope apparatus of FIG. 14, which are a side view and a front view, respectively. FIGS. 17A, 17B, and 17C are explanatory views of essential parts of the structure of the actuation part of the specimen vessel pressing release means in the box-type microscope apparatus of FIG. 14, which are a side view conceptually showing a state of the actuation part where the moving housing is closed; a side view conceptually showing a state of the actuation part where the moving housing is opened; and a partially longitudinal sectional view of FIG. 17A in the actuation part, respectively. Also, like numerals are used for like members with respect to the first embodiment, Specific Embodiment 1, or Specific Embodiment 2.

The box-type microscope apparatus of Specific Embodiment 3 is constructed in almost the same way as Specific Embodiments 1 and 2 with the exception of the structures of a housing 20′′′ and a positioning release means.

The housing 20′′′ is provided with a moving housing 22′′′ on a fixed housing 21′′′ placed on the lower side. The moving housing 22′′′ incorporates all optical elements constituting the transmitting illumination optical system 11, containing the halogen lamp 11$a$, the coupling lens 11$b$, and the optical fiber 11$c$. The moving housing 22′′′ is constructed to be movable parallel to an oblique direction with respect to the fixed housing 21′′′ while holding the transmitting illumination optical system 11 located above the electric stage 12. The housing 20′′′ is constructed so that the moving housing 22′′′ is moved parallel to an oblique upward direction by a preset amount and thereby the fixed housing 21′′′ is opened and the specimen vessel 40 placed on the electric stage 12 is made replaceable, while the moving housing 22′′′ is moved parallel to an oblique downward direction to abut on the fixed housing 21′′′ and thereby the inverted microscope 10 is sealed and light-blocked in cooperation with the fixed housing 21′′′ and the optical axis of the condenser lens 11$f$ is aligned with that of the objective lens 14$a$.

A movement mechanism of the moving housing 22′′′, as shown in FIGS. 16A and 16B, is constructed to have a stand 31, a guide member 32, a rail 33, a motor 34, a toothed pulley 35, a timing belt 36, and idlers 37. The stand 31 is fixed to the fixed housing 21′′′. The guide member 32 is constructed with a guide block of U-shaped cross section, for example, of Model No. SHS 15 by THK CO., LTD., and is fixed to one side 31$a$ of the stand 31 through screws at a preset inclination angle θ with respect to an abutment surface between the fixed housing 21′′′ and the moving house 22′′′ (a horizontal surface in FIG. 14). The rail 33 is fixed to one inside surface 22$a'''$ of the moving housing 22′′′ through a connecting member 33$a$ at the preset inclination angle θ like the above description and is guidably fitted into the guide member 32. The motor 34 includes a pulse motor, for example, of Model No. PK229 by ORIENTAL MOTOR CO., LTD., and is mounted to the stand 31. The toothed pulley 35 is mounted to the motor 34. The timing belt 36 includes the one, for example, of Model No. HTUN 280 by MISUMI Corporation, and it is fixed to the inside surface 22$a'''$ of the moving housing 22′′′ with respect to its both ends 36$a$ and 36$b$ at the preset inclination angle θ like the above description and is engaged with the toothed pulley 35. The idlers 37 are fixed to the stand 31 so as to hold the engagement of the toothed pulley 35 with the timing belt 36.

The movement mechanism of the moving housing 22′′′ also has a rolling member 38 and a second rail 39. The rolling member 38 is constructed with rollers that are rotatable on an axis 38$a$ and is mounted to a remaining inside surface 22$b'''$ of the moving housing 22′′′. The second rail 39 is fixed to a remaining side 31$b$ of the stand 31 at the preset inclination angle θ like the above description and supports the rolling member 38. In addition, the movement mechanism of the moving housing 22′′′ is provided with a well-known brake member (not shown) as a position holding means for holding the position where the moving housing 22′′′ is moved parallel to the oblique direction with respect to the fixed housing 21′′′. The positioning release means has an engagement part, a specimen vessel pressing release means, and an actuation part of the specimen vessel pressing release means (not shown in FIG. 14). The engagement part and the specimen vessel pressing release means are constructed in the same way as the engagement part 61 and the specimen vessel pressing release means 62 shown in FIG. 6.

The actuation part of the specimen vessel pressing release means, as illustrated in FIGS. 17A and 17C, is constructed with a plate-shaped projection 63′′′ having a preset length in a vertical direction, provided to the moving housing 22′′′ and is such that when the moving housing 22′′′ is moved parallel to the oblique direction with respect to the fixed housing 21′′′, a part of the plate-shaped projection 63′′′ pressing the end 62$b^2$ opposite to the pressing part 62$b^1$ of the release lever is displaced along the vertical direction. The actuation part 63′′′ of the specimen vessel pressing release means presses the specimen vessel pressing release means 62 and thereby the pressing of the specimen vessel pressing means 52 on the specimen vessel 40 is released through the specimen vessel pressing release means 62 shown in FIG. 6 so that when the moving housing 22′′′ is located at the position of the opened state with respect to the fixed housing 21′′′, a release from the pressing on the specimen vessel 40 applied by the specimen vessel pressing means 52 is completed through the specimen vessel pressing release means 62.

Other features are nearly the same as in the box-type microscope apparatus of the first embodiment or Specific Embodiment 1 or 2.

In order to use the box-type microscope apparatus of Specific Embodiment 3 constructed as mentioned above to curry out the observation of the specimen, the electric stage 12 is first moved to a preset reference position where the replacement of the specimen vessel becomes possible. Subsequently, the moving housing 22′′′ is moved in the direction of the opened state. In this case, when the operator manually applies a force in the direction of the opened state, the rail 33 is guided by the guide member 32 and the moving housing 22′″ is moved parallel to an axial direction at the preset inclination angle θ with respect to the abutment surface between the fixed housing 21′″ and the moving house 22′″. Also, at this time, the timing belt 36 is pulled in a preset direction and the toothed pulley 35 is rotated through the idlers 37. When the motor 34 is rotated, the toothed pulley 35 is rotated in the direction of rotation of the motor to pull the timing belt 36 in a preset direction through the idlers 37.

Whereby, the rail 33 is guided by the guide member 32 and the moving housing 22′″ is moved parallel to the axial direction at the preset inclination angle θ with respect to the abutment surface between the fixed housing 21′″ and the moving house 22′″. At this time, in accordance with the movement of the moving housing 22′″, the rolling member 80 is rotated on the second rail 39 and at the same time, the moving housing 22′″ is moved parallel to the axial direction at the preset inclination angle θ with respect to the abutment surface between the fixed housing 21′″ and the moving house 22′″. For the direction of the opened state, the moving housing 22′″ can be moved to a preset position where the specimen vessel 40 placed on the electric stage 12 can be replaced. The moving housing 22′″ moved to this preset position is held by the position holding means. Whereby, the operator is capable of replacing the specimen vessel 40.

In this way, when the moving housing 22′″ is moved in the direction of the opened state, as shown in FIG. 17B, the plate-shaped projection constituting the actuation part 63′″ of the specimen vessel pressing release means is moved integrally with the moving housing 22′″ in the direction of an arrow H. When the moving housing 22′″ is moved in the direction of the opened state by a preset amount, the actuation part 63′″ of the specimen vessel pressing release means presses the end 62$b^2$ of the release lever that is the specimen vessel pressing release means 62 while displacing a part of the plate-shaped projection pressing the end 62$b^2$ opposite to the pressing part 62$b^1$ of the release lever in the vertical direction, and as shown in FIG. 6, rotates the lever body 62$b$ on the shaft 62$a$ in the direction of the arrow B against the tensile force of the spring 62$c$. When the moving housing 22′″ reaches the position of the opened state, the release lever 62 presses the engagement part 61 of the clamp lever 52 that is the specimen vessel pressing means, through the pressing part 62$b^1$ and rotates the lever body 52$b$ on the shaft 52$a$ in the direction of the arrow C (in the direction opposite to that of the pressing on the specimen vessel 40) against the tensile force of the spring 52$c$. At this time, the pressing part 52$b^1$ separates from the position where the corner 40$c^1$ of the specimen vessel 40 is pressed. Whereby, the loading and unloading of the specimen vessel 40 onto and from the place surrounded by the frame-shaped member 51 on the electric stage 12 become possible.

After the operator places the specimen vessel 40 incorporating the specimen A on the electric stage 12, the moving housing 22′″ is moved in the direction of the closed state. At this time, the plate-shaped projection constituting the specimen vessel pressing means 63′″ shown in FIG. 17B is moved integrally with the moving housing 22′″ in the direction opposite to that of the arrow H. When the moving housing 22′″ is moved in the direction of the closed state by the preset amount, the actuation part 63′″ of the specimen vessel pressing release means displaces the part of the plate-shaped projection pressing the end 62$b^2$ opposite to the pressing part 62$b^1$ of the release lever along the vertical direction. The pressing of the actuation part 63′″ of the specimen vessel pressing release means on the end 62$b^2$ of the release lever that is the specimen vessel pressing release means 62 is gradually reduced and then is released. When the pressing of the actuation part 63′″ of the specimen vessel pressing release means on the end 62$b^2$ of the release lever is released, the tensile force of the spring 62$c$ shown in FIG. 6 is exerted and the lever body 62$b$ is rotated on the shaft 62$a$ in the direction opposite to that of the arrow B. At this time, the pressing on the engagement part 61 of the clamp lever 52 that is the specimen vessel pressing means, through the pressing part 62$b^1$ of the release lever 62, is released.

Whereby, the tensile force of the spring 52$c$ is exerted and the lever body 52$b$ is rotated on the shaft 52$a$ in the direction opposite to that of the arrow C (in the direction of the arrow D). At this time, the pressing part 52$b^1$ presses the corner 40$c^1$ of the specimen vessel 40. Whereby, the specimen vessel 40 is moved toward the X-direction bumping part 51$a$ and the Y-direction bumping part 51$b$ of the frame-shaped member 51, and the specimen vessel 40 is fixed to a constant position with respect to the electric stage 12 in a state where the side surfaces 40$a$ and 40$b$ abut on the bumping parts 51$a$ and 51$b$, respectively. When the moving housing 22′ is closed, the sensor 27 outputs the detection signal of the closed state. In this state, the transmitting illumination optical system 11 provided to the moving housing 22′″ is located at the position where the optical axis of the condenser lens 11$f$ is aligned with that of the objective lens 14$a$.

Other functions are almost the same as in the box-type microscope apparatus of the first embodiment or Specific Embodiment 1 or 2.

In the box-type microscope apparatus of Specific Embodiment 3 as well, like the box-type microscope apparatus of Specific Embodiment 1, the specimen vessel 40 can be always fixed to a constant position by a simple operation, and the positional adjustment of the specimen vessel 40 becomes unnecessary. In addition, the specimen vessel 40 mounted to the electric stage 12 can be always located at a constant position. As a result, the electric stage 12 is only moved by a constant amount, for example, with a position detected by a position sensor of the electric stage 12 as a reference, and thereby a desired part in the specimen vessel 40 can be located at a correct observation and/or measurement position (namely, a preset position on the optical axis connecting the illumination optical system with the image forming optical system).

Also, although the movement mechanism of the moving housing 22′″ shown in FIGS. 16A and 16B is constructed so that electric driving means, such as the motor 34, the pulley 35, the timing belt 36, and the idlers 37, are provided and thereby the moving housing 22′″ can be electrically driven, it may be constructed so that the moving housing 22′″ is driven only by the manual operation without providing such electric driving means.

Also, each of the embodiments mentioned above is constructed so that the moving housing is manually opened and closed, but it may be such that the moving housing can be automatically opened and closed through a driving means. Further, in the box-type microscope apparatus of each embodiment, the microscope is constructed with the inverted microscope having the reflecting illumination optical system 13, but it is also applicable to an arrangement excluding the reflecting illumination optical system 13.

As will be obvious from the above description, the present invention is useful in the fields of medical treatment, medical science, and biology in which the box-type microscope apparatus is used to observe and/or measure living specimens, such as cells.

What is claimed is:

1. A box-type microscope apparatus, comprising:
a microscope having a stage for placing a specimen vessel thereon, a transmitting illumination optical system, and an image forming optical system;
a housing surrounding the microscope, the housing including a fixed housing and a moving housing provided to be openable, closable, and movable with respect to the fixed housing;
a switching mechanism in which, of optical parts constituting the transmitting illumination optical system or the image forming optical system, at least partial optical parts arranged above the stage are provided to be movable so that when the moving housing is located at a position of an opened state with respect to the fixed housing, the partial optical parts are removed from an optical axis of a remaining optical system, while when the moving housing is located at a position of a closed state, an optical axis of the transmitting illumination optical system is aligned with an optical axis of the image forming optical system;
specimen vessel positioning means for fixing the specimen vessel placed on the stage at a constant position of the stage; and
positioning release means for actuating the specimen vessel positioning means when the moving housing is moved from the position of the opened state toward the position of the closed state with respect to the fixed housing and for releasing a positioning of the specimen vessel performed by the specimen vessel positioning means with respect to the stage when the moving housing is located at the position of the opened state with respect to the fixed housing.

2. A box-type microscope apparatus according to claim 1, wherein the specimen vessel positioning means has a bumping part on which side surfaces of the specimen vessel placed on the stage are allowed to abut from X and Y directions and a specimen vessel pressing means for pressing a preset corner of the specimen vessel placed on the stage to make the side surfaces of the specimen vessel abut on the bumping part.

3. A box-type microscope apparatus according to claim 2, wherein the specimen vessel pressing means is a clamp lever including a shaft provided to the stage; a lever body rotatably supported by the shaft, provided with a pressing part allowing the preset corner of the specimen vessel to be pressed; and a spring whose one end is connected to the lever body and whose remaining end is connected to the stage, applying a force to the lever body in a direction in which the preset corner of the specimen vessel is pressed.

4. A box-type microscope apparatus according to claim 2 or 3, wherein the positioning release means includes an engagement part provided to the specimen vessel pressing means; a specimen vessel pressing release means for pressing the engagement part to be releasable with respect to a pressing of the specimen vessel applied by the specimen vessel pressing means, the specimen vessel pressing release means being provided to a preset part of the housing to allow a pressing; and an actuation part of the specimen vessel pressing release means releasing the pressing on the specimen vessel applied by the specimen vessel pressing means through the specimen vessel pressing release means by pressing the specimen vessel pressing release means so that when the moving housing is located at the position of the opened state with respect to the fixed housing, a release from the pressing on the specimen vessel applied by the specimen vessel pressing means is completed through the specimen vessel pressing release means.

5. A box-type microscope apparatus according to claim 4, wherein the specimen vessel pressing release means is a release lever including a shaft provided to the fixed housing; a lever body rotatably supported by the shaft, provided at one end with a pressing part allowing the engagement part provided to the specimen vessel pressing means to be pressed; and a spring whose one end is connected to the lever body and whose remaining end is connected to the fixed housing, applying a force to the lever body in a direction in which the pressing on the engagement part provided to the specimen vessel pressing means is released, and the actuation part of the specimen vessel pressing release means allows an end opposite to the pressing part of the release lever to be pressed.

6. A box-type microscope apparatus according to claim 4, wherein the specimen vessel pressing release means is a release lever including a shaft provided to the stage; a lever body rotatably supported by the shaft, provided at one end with a pressing part allowing the engagement part provided to the specimen vessel pressing means to be pressed; and a spring whose one end is connected to the lever body and whose remaining end is connected to the stage, applying a force to the lever body in a direction in which a pressing on the engagement part provided to the specimen vessel pressing means is released, and the actuation part of the specimen vessel pressing release means allows an end opposite to the pressing part of the release lever to be pressed.

7. A box-type microscope apparatus according to claim 1 or 2, wherein the moving housing is mounted to be movable in a direction horizontal with respect to the fixed housing.

8. A box-type microscope apparatus according to claim 1 or 2, wherein the moving housing is mounted to be movable parallel to an oblique direction with respect to the fixed housing.

9. A box-type microscope apparatus according to claim 1 or 2, wherein the moving housing is mounted to be rotatable, with a rotary axis as a center, with respect to the fixed housing.

10. A box-type microscope apparatus according to claim 7, wherein an actuation part of a specimen vessel pressing release means includes a projection provided to the moving housing.

11. A box-type microscope apparatus according to claim 8, wherein an actuation part of a specimen vessel pressing release means includes a plate-shaped projection having a preset length in a vertical direction and provided to the moving housing, and when the moving housing is moved parallel to an oblique direction with respect to the fixed housing, a part of the plate-shaped projection pressing an end opposite to a pressing part of a release lever is displaced along a vertical direction.

12. A box-type microscope apparatus according to claim 9, wherein an actuation part of a specimen vessel pressing release means includes a plate-shaped member having a preset length whose one end is mounted to be rotatable on a rotary axis with respect to the moving housing and whose remaining end is mounted to be guidable at least in a horizontal direction through a guide member provided to the fixed housing so that when the moving housing is rotated on a rotary axis with respect to the fixed housing, a part of the plate-shaped member pressing an end opposite to a pressing part of a release lever is displaced along a longitudinal direction.

* * * * *